United States Patent
Gosling et al.

(10) Patent No.: US 7,108,990 B2
(45) Date of Patent: Sep. 19, 2006

(54) CHEMOKINE RECEPTOR

(75) Inventors: Jennifa Gosling, San Francisco, CA (US); Daniel J. Dairaghi, Palo Alto, CA (US); Michael Hanley, Corte Madera, CA (US); Zhenhua Miao, San Jose, CA (US); Thomas J. Schall, Menlo Park, CA (US)

(73) Assignee: ChemoCentryx, Inc., Mountain View, CA (US)

( * ) Notice: Subject to any disclaimer, the term of this patent is extended or adjusted under 35 U.S.C. 154(b) by 164 days.

(21) Appl. No.: 10/787,018

(22) Filed: Feb. 24, 2004

(65) Prior Publication Data

US 2004/0146926 A1    Jul. 29, 2004

Related U.S. Application Data

(63) Continuation of application No. 09/721,495, filed on Nov. 21, 2000, now Pat. No. 6,835,547, which is a continuation of application No. 09/686,019, filed on Oct. 10, 2000, now abandoned.

(60) Provisional application No. 60/186,626, filed on Mar. 3, 2000, provisional application No. 60/173,388, filed on Dec. 28, 1999, provisional application No. 60/172,979, filed on Dec. 20, 1999, provisional application No. 60/159,210, filed on Oct. 13, 1999, provisional application No. 60/159,015, filed on Oct. 12, 1999.

(51) Int. Cl.
*G01N 33/53* (2006.01)
*G01N 33/566* (2006.01)

(52) U.S. Cl. ............................................. 435/7.2
(58) Field of Classification Search ............... None
See application file for complete search history.

(56) References Cited

U.S. PATENT DOCUMENTS

| | | | |
|---|---|---|---|
| 5,932,445 A | 8/1999 | Lal et al. | |
| 6,110,695 A | 8/2000 | Gunn et al. | |
| 2001/0016336 A1 | 8/2001 | Ellis | |

FOREIGN PATENT DOCUMENTS

| | | |
|---|---|---|
| EP | 0 899 332 A2 | 3/1999 |
| WO | WO 99/24463 A2 | 5/1999 |
| WO | WO 99/33876 A1 | 7/1999 |
| WO | WO 99/52945 A2 | 10/1999 |
| WO | WO 00/26369 A1 | 5/2000 |
| WO | WO 00/64941 A2 | 11/2000 |

OTHER PUBLICATIONS

U.S. Appl. No. 09/686,020, Gosling et al.
U.S. Appl. No. 09/721,341, Gosling et al.
U.S. Appl. No. 09/686,019, Gosling et al.
U.S. Appl. No. 09/721,495, Gosling et al.
Database EMBL Accession No. Q9NPB9; Oct. 1, 2000.
Database EMBL Accession No. Y30125; Oct. 14, 1999.
GenBank Accession No. AA215577; Aug. 13, 1997.
GenBank Accession No. AF233281; May. 22,2000.
GenBank Accession No. AI131555; Oct. 26, 1998.
GenBank Accession No. AI769466; Jun. 28, 1999.
GenBank Accession No. AR003970; Dec. 10, 1998.
GenBank Accession No. AW190975; Nov. 22, 1999.
GenBank Accession No. E12852; Jun. 24, 1998.
GenBank Accession No. H67224; Oct. 27, 1995.
Baggiolini, M. "Chemokines in pathology and medicine." Journal Internal Medicine, 2001, pp. 91-104, vol. 250.
Bork, Peer, et al., Go hunting in sequence databases but watch out for the traps; *Trends in Genetics*; Oct. 1996; pp. 425-427; vol. 12, No. 10.
Bork, Peer; Powers and Pitfalls in Sequence Analysis: The 70% Hurdle; *Genome Research*2000; pp. 398-400; vol. 10.
Brenner, Steven E.; Errors in genome annotation; *Trends in Genetics*; Apr. 1999; pp. 132-133; vol. 15, No. 4.
Dairaghi, Daniel J.;, et al. Chemokine Receptor CCR3 Function Is Highly Dependent on Local pH and Ionic Strength; The Journal of Biological Chemistry; Nov. 7, 1997; pp. 28206-28209; vol. 272, No. 45.
Dairaghi, Daniel J. et al.; HHV8-encoded vMIP-I Selectively Engages Chemokine Receptor CCR8; The Journal of Biological Chemistry; Jul. 30, 1999; pp. 21569-21574; vol. 274, No. 31.
Doerks, Tobias, et al.; Protein annotation; detective work for function prediction; *Trends in Genetics*; Jun. 1998; pp. 248-250; vol. 14, No. 6.
Gosling, Jennifa, et al., Cutting Edge: Identification of a Novel Chemokine Receptor That Binds Dendritic Cell-and T Cell-Active Chemokines Including ELC, SLC, and TECK; The Journal of Immunology; 2000; pp. 2851-2856.
Khoja, Hamiduddin, et al., Cloning of CCRL1, an orphan seven transmembrane receptor related to chemokine receptors, expressed abundantly in the heart; *Gene*; 2000; pp. 229-238; vol. 246.
Hulme, E.C., editor, Receptor-Ligand Interactions A Practical Approach; 1992; Preface, Table of Contents, Chapters 6,7,8 and 9; pp. viii-xv and 213-263; IRL Press at Oxford University Press Inc., New York, New York.
Matsuoka, Ichiro et al.; Identification of Novel Members of G-Protein Coupled Receptor Superfamily Expressed in Bovine Taste Tissue; Biochemical and Biophysical Research Communications; Jul. 15, 1993; pp. 504-511; vol. 194, No. 1.

(Continued)

*Primary Examiner*—Michael Pak
(74) *Attorney, Agent, or Firm*—Townsend and Townsend and Crew LLP

(57) ABSTRACT

The invention provides polypeptides and polynucleotides encoding a novel chemokine receptor, CCX CKR. The invention further provides reagents and methods for identifying agents that modulate the activity or expression of the receptors, as well as methods for detecting receptor expression.

14 Claims, 10 Drawing Sheets

OTHER PUBLICATIONS

Murphy, P. "International Union of Pharmacology, XXX. Update on Chemokine Receptor Nomenclature" Pharmacological Reviews, 2002, pp. 227-229, vol. 54, USA.

Ngo, J. Thomas, et al; Computational Complexity, Protein Structure Prediction and the Levinthal Paradox; *The Protein Folding Problem and Tertiary Structure Prediction*, K. Merz, Jr. and S. LeGrand, Editors; 1994; pp. 491-495; Birkhauser, Boston.

O'Dowd, Brian F., et al.; A novel gene codes for a putative G protein-coupled receptor with an abundant expression in brain; FEBS Letters 1996; pp. 325-329.

Schweickart, Vicki L. et al.; CCR11 Is a Functional Receptor for the Monocyte Chemoattractant Protein Family of Chemokines; The Journal of Biological Chemistry; Mar. 31, 2000; pp. 9550-9556; vol. 275, No. 13.

Sissors, Daniel L., et al.; A Homogeneous Receptor Binding Assay for HTS on FlashPlate® Plus; NEN® Life Science Products, Inc.; 1999; pp. 1-7.

Skolnick, Jeffrey, et al; From gene to protein structure and function: novel applications fo computational approaches in the genomic era; *Trends in Biotech*; 2000; pp. 34-39; vol. 18, No. 1.

Smith, Temple F., et al.; The challenges of genome sequence annotation or "The devil is in the details"; *Nature Biotechnolgy*; Nov. 1997; pp. 1222-1223; vol. 15.

Townson, Jane R., et al.; Characterization of mouse CCX-CKR, a receptor for the lymphocyte-attracting chemokines TECK/mCCL25, SLC/mCCL21 and MIP-3β/mCCL 19: comparison to human CCX-CKR; *Eur. J. Immunol*, 2002; pp. 1230-1241; vol. 32.

Wells, James A.; Additivity of Mutational Effects in Proteins; *Biochemistry*; Sep. 18, 1990; pp. 8509-8517; vol. vol. 29, No. 37.

```
ATGGCTTTGG AACAGAACCA GTCAACAGAT TATTATTATG AGGAAAATGA    50
 M  A  L  E   Q  N  Q    S  T  D   Y  Y  Y   E  E  N  E

AATGAATGGC ACTTATGACT ACAGTCAATA TGAACTGATC TGTATCAAAG   100
 M  N  G   T  Y  D  Y   S  Q  Y   E  L  I    C  I  K  E

AAGATGTCAG AGAATTTGCA AAAGTTTTCC TCCCTGTATT CCTCACAATA   150
  D  V  R   E  F  A    K  V  F    L  P  V  F   L  T  I

GTTTTCGTCA TTGGACTTGC AGGCAATTCC ATGGTAGTGG CAATTTATGC   200
 V  F  V  I   G  L  A   G  N  S   M  V  V  A   I  Y  A

CTATTACAAG AAACAGAGAA CCAAAACAGA TGTGTACATC CTGAATTTGG   250
 Y  Y  K    K  Q  R  T   K  T  D   V  Y  I   L  N  L  A

CTGTAGCAGA TTTACTCCTT CTATTCACTC TGCCTTTTTG GGCTGTTAAT   300
 V  A  D   L  L  L    L  F  T  L   P  F  W    A  V  N

GCAGTTCATG GGTGGGTTTT AGGGAAAATA ATGTGCAAAA TAACTTCAGC   350
 A  V  H  G   W  V  L   G  K  I    M  C  K  I   T  S  A

CTTGTACACA CTAAACTTTG TCTCTGGAAT GCAGTTTCTG GCTTGTATCA   400
 L  Y  T    L  N  F  V   S  G  M   Q  F  L    A  C  I  S

GCATAGACAG ATATGTGGCA GTAACTAAAG TCCCCAGCCA ATCAGGAGTG   450
  I  D  R   Y  V  A    V  T  K  V   P  S  Q   S  G  V

GGAAAACCAT GCTGGATCAT CTGTTTCTGT GTCTGGATGG CTGCCATCTT   500
 G  K  P  C   W  I  I   C  F  C    V  W  M  A   A  I  L

GCTGAGCATA CCCCAGCTGG TTTTTTATAC AGTAAATGAC AATGCTAGGT   550
 L  S  I    P  Q  L  V   F  Y  T   V  N  D    N  A  R  C

GCATTCCCAT TTTCCCCCGC TACCTAGGAA CATCAATGAA AGCATTGATT   600
 I  P  I    F  P  R    Y  L  G  T   S  M  K    A  L  I

CAAATGCTAG AGATCTGCAT TGGATTTGTA GTACCCTTTC TTATTATGGG   650
 Q  M  L  E   I  C  I   G  F  V    V  P  F  L   I  M  G

GGTGTGCTAC TTTATCACAG CAAGGACACT CATGAAGATG CCAAACATTA   700
 V  C  Y    F  I  T  A   R  T  L   M  K  M    P  N  I  K

AAATATCTCG ACCCCTAAAA GTTCTGCTCA CAGTCGTTAT AGTTTTCATT   750
  I  S  R   P  L  K    V  L  L  T   V  V  I   V  F  I

GTCACTCAAC TGCCTTATAA CATTGTCAAG TTCTGCCGAG CCATAGACAT   800
 V  T  Q  L   P  Y  N   I  V  K    F  C  R  A   I  D  I

CATCTACTCC CTGATCACCA GCTGCAACAT GAGCAAACGC ATGGACATCG   850
 I  Y  S    L  I  T  S   C  N  M   S  K  R    M  D  I  A

CCATCCAAGT CACAGAAAGC ATCGCACTCT TTCACAGCTG CCTCAACCCA   900
 I  Q  V    T  E  S    I  A  L  F   H  S  C    L  N  P

ATCCTTTATG TTTTTATGGG AGCATCTTTC AAAAACTACG TTATGAAAGT   950
 I  L  Y  V   F  M  G   A  S  F    K  N  Y  V   M  K  V

GGCCAAGAAA TATGGGTCCT GGAGAAGACA GAGACAAAGT GTGGAGGAGT  1000
 A  K  K    Y  G  S  W   R  R  Q   R  Q  S    V  E  E  F

TTCCTTTTGA TTCTGAGGGT CCTACAGAGC CAACCAGTAC TTTTAGCATT  1050
 P  F  D    S  E  G    P  T  E  P   T  S  T   F  S  I

TAAAGGTAAA ACTGCTCTGC CTTTTGCTTG GATACATATG AATGATGCTT  1100
 -  R  -  N   C  S  A   F  C  L    D  T  Y  E   -  C  F

TCCCCTCAAA TAAACATCT GCCTTATTCT GAAAAAAAAA AAAAAM       1147
 P  L  K    -  N  I  C   L  I  L   K  K  K    K  K
```

FIG. 1

```
CCX-CKR        MALEQNQSTDYYE--ENEMNGTY-------DYSQYELICIK   33
CCR9           MTPTDFTSPIPNMADDYG-SESTSSM-EDYVN----FNFTDF---YCEK
CCR7    MDLGKPMKSVLVVALLVIFQVCLCQDEVTDDYIGDNTTVDYTLFESLCSK
CCR6           MSGESMNFSDVFDSSEDYFVS-----VNTSMYS----VDSEML---LCSL
STRL33         MAEHDYHEDYGFS---------SF-NDSSQEEHQDF--L---
```

TM1

```
CCX-CKR   EDVREFAKVFLBVFLTIVFVIGDAGNSMVVAIYAYYKKQRTKTDVYILNL   83
CCR9      NNVRQFASHFLPPLYWLVEIVGALGNSLMILVWYCTRVKTMTDMFLLNL
CCR7      KDVRNFKAWFLPIMYSIICFVGLLGNGLVVLTYIYFKRLKTMTDTYLLNL
CCR6      QEVBQFSRLFVPIAYSLICVFGLLGNILVVITFAFYKKARSMTDVYILNM
STRL33    ----QESKVFLBCMYLVVFVCGLVGNSLMLVISIFMHSLQSLTDVFLVNL
```

TM2                                    TM3

```
CCX-CKR   AMADLLLLFTLPFWAV-NAVHGWVLGKIMCKITSALYTLNFVSGMQFLAC  132
CCR9      ATADLLFLVTLPFWAIA-ADQWKFQTFMCKVVNSMYKMNFYSCVLLIMC
CCR7      AMADILFLLTLPFWAYS-AAKSWVFGVHFCKLIFAIYKMSFFSGMLLLC
CCR6      AIADILFVLTLPFWAVSHATGAWVFSNATCKLLKGIYAINFNCGMLLLT
STRL33    PLADLVFVCTLPFWAYA-GIHEWVFGQVMCKSLLGIYTINFYTSMLILTC
```

TM4

```
CCX-CKR   ISIDRYVAVTK-VPSQSGVGKP---CWIICFCVWMAAILLSIBQLVFYTV  178
CCR9      ISMDRYIAIAQAMRAHTWREKRLLYSKMVCFTIWVLAAALCIBEILYSQI
CCR7      ISIDRYVAIVQAVSAHRHRARVLLISKLSCVGSAILAFVLSIBELLYSDL
CCR6      ISMDRYIAIVQATKSFRLRSRTLPRTKIIQLVVWGLSVIISSSTFVFNQK
STRL33    ITVDEFIVVVKATKAYNQQAKRMTWGKVTSLLIWVISLLVSLEQIIYGNV
```

TM5

```
CCX-CKR   NDNAR---CIPIFPRY-LGTSMKALIQMLEICIGFVVPFLIMGVCYFITA  224
CCR9      KEESGIAICTMVYPS-DESTKLKSAVLTLKVILGFFLPFVVMACCYTIII
CCR7      QRSSSEQAMRCSLIT-EHVEAF-ITIQVAQMVIGFLVPLLAMSFCYLVII
CCR6      YNTQGSDVCEPKYQTVSEPIRWKLLMLGLELLFGFFIPLMFMIFCYTFIV
STRL33    FNLDKL-IC--GYH--DEAIS--TVVLATQMTLGFFLPLLTMIVCYSVII
```

TM6

```
CCX-CKR   RTLMKMPNIKISREAKVLLTVVIVFIVTQLPYNLVKFCRAIDIIYSLITS  274
CCR9      HTLIQAKKSSKHKALKVTITVLTVFVLSQFPYNCILLVQTIDAYAMFISN
CCR7      RTLLQARNFERNKAIKVIIAVVMVFIVFQLPYNGVVLAQTVANFNITSST
CCR6      KTLVQAQNSKRHKAIRMIIAVVLVFLACQIPHNMVLLV-TAANLGKMNRS
STRL33    KTLLHAGGFQKHRSLKIIFLVMAVFLLTQMPFNLMKFIRSTH------WE
```

FIG. 2A

```
                            TM7
CCX-CKR   CNMSKRMDIAIQVTESIALFHSCLNEILYVFMGASFKNYVMK-------V  317
CCR9      CAVSTNIDICFQVTQTIAFFHSCLNEVLYVFVGERFRRDLVKTLKNLGCI
CCR7      CELSKQLNIAYDVTYSLACVRCCVNEFLYAFIGVKFRNDIFKLFKDLGCL
CCR6      CQSEKLIGYTKTVTEVLAFLHCCLNEVLYAFIGQKFRNYFLKILKDLWCV
STRL33    YYAMTSFHYTIMVTEAIAYLRACLNEVLYAFVSLKFRKNFWKLVKDIGCL

CCX-CKR   AKKV--GSWRRQRQSVEEFPFDSEGP--TEFTSTFSI                350
CCR9      SQA-QWVSFTR----REGSLK-LSSMLLETTSGALSL
CCR7      SQE-QLRQWSS----CRHIRR-SSMSVEAETITTFSP
CCR6      RRKYKSSGFSCAGRYSENISRQTSETADNDNASSFTM
STRL33    P--Y--LGVSHQWKSSEDNSKTFSASHNVEATSMFQL
```

*FIG. 2A*
(CONTINUED)

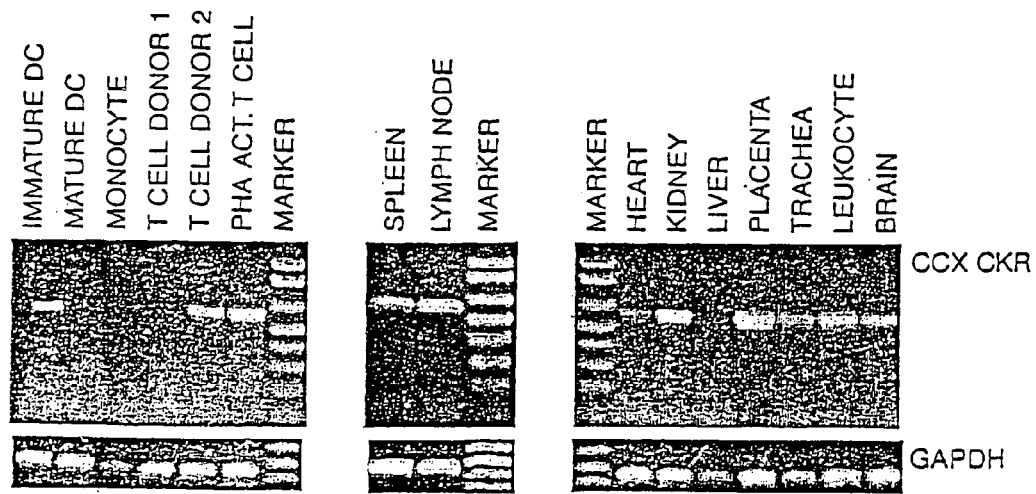

*FIG. 2B*

```
5'upstream   ATGCAGCATC TCGTTTATAA AAGGCAACTA GTGAAATTTA GTGCAAATGC    50
CCXCKR       ---------- ---------- ---------- ---------- ----------

5'upstream   TGAGAGAATT TATTTAACTT ATTTAAATTA AATTTATAAA TAACATCAAA   100
CCXCKR       ---------- ---------- ---------- ---------- ----------

5'upstream   ATAAAAAATA AATTTAATTT AAATAAACCA AGTAATTTGC TATTTTCGTT   150
CCXCKR       ---------- ---------- ---------- ---------- ----------

5'upstream   TTTATTCAAT TTGTTGTAGA TATACTTTTA CGATTCACAA AATTATGTAT   200
CCXCKR       ---------- ---------- ---------- ---------- ----------

5'upstream   GTAAAGATTA TAACACTATT TATTCTTTTT AGTTAAAATC TAATTAAATT   250
CCXCKR       ---------- ---------- ---------- ---------- ----------

5'upstream   TTCATATTTT AAAAATCATT TTTACATAAA AGTCTTCACT TTTATTTAGG   300
CCXCKR       ---------- ---------- ---------- ---------- ----------

5'upstream   ATTTAATGAT TAAGAAAATT CTCCAGGGCA TTATGTTTAT TGTCCTGTTC   350
CCXCKR       ---------- ---------- ---------- ---------- ----------

5'upstream   AAATCCAAGC TCTTTCACAC AGAATTGTAC AAGCAAAGTT TGAGTAACTA   400
CCXCKR       ---------- ---------- ---------- ---------- ----------

5'upstream   ATCTTGGGGT CATATTCCAA TGTGGCTCCC ATTAAAGCAT TCAAAGAGT    450
CCXCKR       ---------- ---------- ---------- ---------- ----------

5'upstream   GCTAGATTCA GGCTCACATA TGTTACAGCA ACAGGCTATA CTCTAGGGAA   500
CCXCKR       ---------- ---------- ---------- ---------- ----------

5'upstream   AGAACAAAAC AGCTTGATAG AAACTGTGTG CTTTTAAGCA TATTTAGACA   550
CCXCKR       ---------- ---------- ---------- ---------- ----------
                                          TRANSLATION START
5'upstream   AATATCTATC CTGTATTCTC TTTGCCATCT AGATTGGAGC CATGGCTTTG   600
CCXCKR       ---------- ---------- ---------- ---------- -ATGGCTTTG     9

5'upstream   GAACAGAACC -GTCAACAGA TTATTATTAT GAGGAGAAGT GAAATGAATG   649
CCXCKR       GAACAGAACC AGTCAACAGA TTATTATTAT GAGGA-AAAT GAAATGAATG    58

5'upstream   GC-CTGATGA CTACAGTCAG TATGAACTGA TCTGT----- --------TC   685
CCXCKR       GCACTTATGA CTACAGTCAA TATGAACTGA TCTGTATCAA AGAAGATCTC   108

5'upstream   AGAGAAGAGA CAGAGGATAT GC-AAAGGGT TGCTCCCTGT ATTGCTCAGC   734
CCXCKR       AGAGAA---- -------TTT GGAAAAGTTT -TCCTCCCTGT ATTCCTCACA   147

5'upstream   ATAG------ ---------- ---------- --------AG ----------   740
CCXCKR       ATAGTTTTCG TCATTGGACT TGCAGGCAAT TCCATGGTAG TGGCAATTTA   197

5'upstream   ---------- ---------- ---------- ---------- ----------   740
CCXCKR       TGCCTATTAC AAGAAACAGA GAACCAAAAC AGATGTGTAC ATCCTGAATT   247

5'upstream   ---------- ---------- ---------- ---------- ----------   740
CCXCKR       TGGCTGTAGC AGATTTACTC CTTCTATTCA CTCTGCCTTT TTGGGCTGTT   297

5'upstream   ---------- ---------- ---------- ---------- ----------   740
CCXCKR       AATGCAGTTC ATGGGTGGGT TTTAGGGAAA ATAATGTGCA AATAACTTC    347
```

FIG. 5

SEQUENCE LISTING

<160> NUMBER OF SEQ ID NOS: 14

<210> SEQ ID NO 1
<211> LENGTH: 1147
<212> TYPE: DNA
<213> ORGANISM: Homo sapiens
<220> FEATURE:
<221> NAME/KEY: CDS
<222> LOCATION: (1)..(1053)
<220> FEATURE:
<223> OTHER INFORMATION: chemokine receptor CCX CKR

<400> SEQUENCE: 1

```
atg gct ttg gaa cag aac cag tca aca gat tat tat tat gag gaa aat        48
Met Ala Leu Glu Gln Asn Gln Ser Thr Asp Tyr Tyr Tyr Glu Glu Asn
  1               5                  10                  15 gaa atg aat ggc act tat gac tac agt caa tat gaa ctg atc tgt atc        96
Glu Met Asn Gly Thr Tyr Asp Tyr Ser Gln Tyr Glu Leu Ile Cys Ile
             20                  25                  30 aaa gaa gat gtc aga gaa ttt gca aaa gtt ttc ctc cct gta ttc ctc       144
Lys Glu Asp Val Arg Glu Phe Ala Lys Val Phe Leu Pro Val Phe Leu
         35                  40                  45 aca ata gtt ttc gtc att gga ctt gca ggc aat tcc atg gta gtg gca       192
Thr Ile Val Phe Val Ile Gly Leu Ala Gly Asn Ser Met Val Val Ala
     50                  55                  60 att tat gcc tat tac aag aaa cag aga acc aaa aca gat gtg tac atc       240
Ile Tyr Ala Tyr Tyr Lys Lys Gln Arg Thr Lys Thr Asp Val Tyr Ile
 65                  70                  75                  80 ctg aat ttg gct gta gca gat tta ctc ctt cta ttc act ctg cct ttt       288
Leu Asn Leu Ala Val Ala Asp Leu Leu Leu Leu Phe Thr Leu Pro Phe
                 85                  90                  95 tgg gct gtt aat gca gtt cat ggg tgg gtt tta ggg aaa ata atg tgc       336
Trp Ala Val Asn Ala Val His Gly Trp Val Leu Gly Lys Ile Met Cys
            100                 105                 110 aaa ata act tca gcc ttg tac aca cta aac ttt gtc tct gga atg cag       384
Lys Ile Thr Ser Ala Leu Tyr Thr Leu Asn Phe Val Ser Gly Met Gln
        115                 120                 125 ttt ctg gct tgt atc agc ata gac aga tat gtg gca gta act aaa gtc       432
Phe Leu Ala Cys Ile Ser Ile Asp Arg Tyr Val Ala Val Thr Lys Val
    130                 135                 140 ccc agc caa tca gga gtg gga aaa cca tgc tgg atc atc tgt ttc tgt       480
Pro Ser Gln Ser Gly Val Gly Lys Pro Cys Trp Ile Ile Cys Phe Cys
145                 150                 155                 160 gtc tgg atg gct gcc atc ttg ctg agc ata ccc cag ctg gtt ttt tat       528
Val Trp Met Ala Ala Ile Leu Leu Ser Ile Pro Gln Leu Val Phe Tyr
                165                 170                 175 aca gta aat gac aat gct agg tgc att ccc att ttc ccc cgc tac cta       576
```

-continued

```
Thr Val Asn Asp Asn Ala Arg Cys Ile Pro Ile Phe Pro Arg Tyr Leu
            180                 185                 190 gga aca tca atg aaa gca ttg att caa atg cta gag atc tgc att gga        624
Gly Thr Ser Met Lys Ala Leu Ile Gln Met Leu Glu Ile Cys Ile Gly
            195                 200                 205 ttt gta gta ccc ttt ctt att atg ggg gtg tgc tac ttt atc aca gca        672
Phe Val Val Pro Phe Leu Ile Met Gly Val Cys Tyr Phe Ile Thr Ala
        210                 215                 220 agg aca ctc atg aag atg cca aac att aaa ata tct cga ccc cta aaa        720
Arg Thr Leu Met Lys Met Pro Asn Ile Lys Ile Ser Arg Pro Leu Lys
225                 230                 235                 240 gtt ctg ctc aca gtc gtt ata gtt ttc att gtc act caa ctg cct tat        768
Val Leu Leu Thr Val Val Ile Val Phe Ile Val Thr Gln Leu Pro Tyr
                245                 250                 255 aac att gtc aag ttc tgc cga gcc ata gac atc atc tac tcc ctg atc        816
Asn Ile Val Lys Phe Cys Arg Ala Ile Asp Ile Ile Tyr Ser Leu Ile
            260                 265                 270 acc agc tgc aac atg agc aaa cgc atg gac atc gcc atc caa gtc aca        864
Thr Ser Cys Asn Met Ser Lys Arg Met Asp Ile Ala Ile Gln Val Thr
        275                 280                 285 gaa agc atc gca ctc ttt cac agc tgc ctc aac cca atc ctt tat gtt        912
Glu Ser Ile Ala Leu Phe His Ser Cys Leu Asn Pro Ile Leu Tyr Val
    290                 295                 300 ttt atg gga gca tct ttc aaa aac tac gtt atg aaa gtg gcc aag aaa        960
Phe Met Gly Ala Ser Phe Lys Asn Tyr Val Met Lys Val Ala Lys Lys
305                 310                 315                 320 tat ggg tcc tgg aga aga cag aga caa agt gtg gag gag ttt cct ttt       1008
Tyr Gly Ser Trp Arg Arg Gln Arg Gln Ser Val Glu Glu Phe Pro Phe
                325                 330                 335 gat tct gag ggt cct aca gag cca acc agt act ttt agc att taa            1053
Asp Ser Glu Gly Pro Thr Glu Pro Thr Ser Thr Phe Ser Ile
            340                 345                 350 aggtaaaaact gctctgcctt ttgcttggat acatatgaat gatgctttcc cctcaaataa    1113
aacatctgcc ttattctgaa aaaaaaaaaa aaam                                  1147

<210> SEQ ID NO 2
<211> LENGTH: 350
<212> TYPE: PRT
<213> ORGANISM: Homo sapiens
<220> FEATURE:
<223> OTHER INFORMATION: chemokine receptor CCX CKR

<400> SEQUENCE: 2

Met Ala Leu Glu Gln Asn Gln Ser Thr Asp Tyr Tyr Glu Glu Asn
 1               5                  10                  15

Glu Met Asn Gly Thr Tyr Asp Tyr Ser Gln Tyr Glu Leu Ile Cys Ile
            20                  25                  30

Lys Glu Asp Val Arg Glu Phe Ala Lys Val Phe Leu Pro Val Phe Leu
        35                  40                  45

Thr Ile Val Phe Val Ile Gly Leu Ala Gly Asn Ser Met Val Val Ala
    50                  55                  60

Ile Tyr Ala Tyr Tyr Lys Lys Gln Arg Thr Lys Thr Asp Val Tyr Ile
65                  70                  75                  80

Leu Asn Leu Ala Val Ala Asp Leu Leu Leu Phe Thr Leu Pro Phe
                85                  90                  95

Trp Ala Val Asn Ala Val His Gly Trp Val Leu Gly Lys Ile Met Cys
            100                 105                 110

Lys Ile Thr Ser Ala Leu Tyr Thr Leu Asn Phe Val Ser Gly Met Gln
```

-continued

```
                     115                 120                 125
Phe Leu Ala Cys Ile Ser Ile Asp Arg Tyr Val Ala Val Thr Lys Val
        130                 135                 140

Pro Ser Gln Ser Gly Val Gly Lys Pro Cys Trp Ile Ile Cys Phe Cys
145                 150                 155                 160

Val Trp Met Ala Ala Ile Leu Leu Ser Ile Pro Gln Leu Val Phe Tyr
                165                 170                 175

Thr Val Asn Asp Asn Ala Arg Cys Ile Pro Ile Phe Pro Arg Tyr Leu
            180                 185                 190

Gly Thr Ser Met Lys Ala Leu Ile Gln Met Leu Glu Ile Cys Ile Gly
        195                 200                 205

Phe Val Val Pro Phe Leu Ile Met Gly Val Cys Tyr Phe Ile Thr Ala
    210                 215                 220

Arg Thr Leu Met Lys Met Pro Asn Ile Lys Ile Ser Arg Pro Leu Lys
225                 230                 235                 240

Val Leu Leu Thr Val Val Ile Val Phe Ile Val Thr Gln Leu Pro Tyr
                245                 250                 255

Asn Ile Val Lys Phe Cys Arg Ala Ile Asp Ile Ile Tyr Ser Leu Ile
            260                 265                 270

Thr Ser Cys Asn Met Ser Lys Arg Met Asp Ile Ala Ile Gln Val Thr
        275                 280                 285

Glu Ser Ile Ala Leu Phe His Ser Cys Leu Asn Pro Ile Leu Tyr Val
    290                 295                 300

Phe Met Gly Ala Ser Phe Lys Asn Tyr Val Met Lys Val Ala Lys Lys
305                 310                 315                 320

Tyr Gly Ser Trp Arg Arg Gln Arg Gln Ser Val Glu Glu Phe Pro Phe
                325                 330                 335

Asp Ser Glu Gly Pro Thr Glu Pro Thr Ser Thr Phe Ser Ile
            340                 345                 350

<210> SEQ ID NO 3
<211> LENGTH: 1147
<212> TYPE: DNA
<213> ORGANISM: Homo sapiens
<220> FEATURE:
<223> OTHER INFORMATION: chemokine receptor CCX CKR (variant)

<400> SEQUENCE: 3
atggctttgg aacagaacca gtcaacagat tattattatg aggaaagtga aatgaatggc     60
actgatgact acagtcagta tgaactgatc tgtatcaaag aagatgtcag agaatttgcc    120
aaagttttcc cccctgtatt cctcacaata gttttcgtca ttggacttgc aggcaattcc    180
atggtagtgc aatttatgc ctattacaag aaacagagaa ccaaaacaga tgtgtacatc    240
ctgaatttgg ctgtagcaga tttactcctt ctattcactc tgccttttg ggctgttaat    300 gcagttcatg ggtgggtttt agggaaaata atgtgcaaaa taacttcagc cttgtacaca    360
ctaaactttg tctctggaat gcagtttctg gcttgtatca gcatagacag atatgtggca    420
gtaactaaag tccccagcca atcaggagtg ggaaaaccat gctggatcat ctgtttctgt    480
gtctggatgg ctgccatctt gctgagcata ccccagctgg ttttttatac agtaaatgac    540
aatgttaggt gcattcccat tttcccccgc aacttaggaa catcaatgaa agcattgatt    600
caaatgctag agatctgcat tggatttgta gtaccctttc ttattatggg ggtgtgctac    660
tttatcacag caaggacact catgaagatg ccaaacatta aaatatctcg acccctaaaa    720
gttctgctca cagtcgttat agttttcatt gtcactcaac tgccttataa cattgtcaag    780
```

```
ttctgccgag ccatagacat catctactcc ctgatcacca gctgcaacat gagcaaacgc    840
atggacatcg ccatccaagt cacagaaagc atcgcactct ttcacagctg cctcaaccca    900
atcctttatg ttttttatggg agcatctttc aaaaactacg ttatgaaagt ggccaagaaa   960
tatgggtcct ggagaagaca gagacaaagt gtggaggagt ttcctttga ttctgagggt    1020 cctacagagc caaccagtac ttttagcatt taaaggtaaa actgctctgc cttttgcttg   1080
gatacatatg aatgatgctt tcccctcaaa taaaacatct gccttattct gaaaaaaaaa   1140 aaaaaam                                                             1147
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 4
aatttggctg tagcagattt actcc                                          25

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 5
gctaaaagta ctggttggc                                                 19

<210> SEQ ID NO 6
<211> LENGTH: 369
<212> TYPE: PRT
<213> ORGANISM: Homo sapiens
<220> FEATURE:
<223> OTHER INFORMATION: chemokine receptor CCR9

<400> SEQUENCE: 6

```
Met Thr Pro Thr Asp Phe Thr Ser Pro Ile Pro Asn Met Ala Asp Asp
 1               5                  10                  15

Tyr Gly Ser Glu Ser Thr Ser Ser Met Glu Asp Tyr Val Asn Phe Asn
                20                  25                  30

Phe Thr Asp Phe Tyr Cys Glu Lys Asn Asn Val Arg Gln Phe Ala Ser
            35                  40                  45

His Phe Leu Pro Pro Leu Tyr Trp Leu Val Phe Ile Val Gly Ala Leu
        50                  55                  60

Gly Asn Ser Leu Val Ile Leu Val Tyr Trp Tyr Cys Thr Arg Val Lys
65                  70                  75                  80

Thr Met Thr Asp Met Phe Leu Leu Asn Leu Ala Ile Ala Asp Leu Leu
                85                  90                  95

Phe Leu Val Thr Leu Pro Phe Trp Ala Ile Ala Ala Ala Asp Gln Trp
            100                 105                 110

Lys Phe Gln Thr Phe Met Cys Lys Val Val Asn Ser Met Tyr Lys Met
        115                 120                 125

Asn Phe Tyr Ser Cys Val Leu Leu Ile Met Cys Ile Ser Val Asp Arg
    130                 135                 140

Tyr Ile Ala Ile Ala Gln Ala Met Arg Ala His Thr Trp Arg Glu Lys
145                 150                 155                 160
```

```
Arg Leu Leu Tyr Ser Lys Met Val Cys Phe Thr Ile Trp Val Leu Ala
                165                 170                 175

Ala Ala Leu Cys Ile Pro Glu Ile Leu Tyr Ser Gln Ile Lys Glu Glu
            180                 185                 190

Ser Gly Ile Ala Ile Cys Thr Met Val Tyr Pro Ser Asp Glu Ser Thr
        195                 200                 205

Lys Leu Lys Ser Ala Val Leu Thr Leu Lys Val Ile Leu Gly Phe Phe
    210                 215                 220

Leu Pro Phe Val Val Met Ala Cys Cys Tyr Thr Ile Ile His Thr
225                 230                 235                 240

Leu Ile Gln Ala Lys Lys Ser Lys His Lys Ala Leu Lys Val Thr
                245                 250                 255

Ile Thr Val Leu Thr Val Phe Val Leu Ser Gln Phe Pro Tyr Asn Cys
                260                 265                 270

Ile Leu Leu Val Gln Thr Ile Asp Ala Tyr Ala Met Phe Ile Ser Asn
            275                 280                 285

Cys Ala Val Ser Thr Asn Ile Asp Ile Cys Phe Gln Val Thr Gln Thr
        290                 295                 300

Ile Ala Phe Phe His Ser Cys Leu Asn Pro Val Leu Tyr Val Phe Val
305                 310                 315                 320

Gly Glu Arg Phe Arg Arg Asp Leu Val Lys Thr Leu Lys Asn Leu Gly
                325                 330                 335

Cys Ile Ser Gln Ala Gln Trp Val Ser Phe Thr Arg Arg Glu Gly Ser
                340                 345                 350

Leu Lys Leu Ser Ser Met Leu Leu Glu Thr Thr Ser Gly Ala Leu Ser
            355                 360                 365

Leu

<210> SEQ ID NO 7
<211> LENGTH: 378
<212> TYPE: PRT
<213> ORGANISM: Homo sapiens
<220> FEATURE:
<223> OTHER INFORMATION: chemokine receptor CCR7

<400> SEQUENCE: 7

Met Asp Leu Gly Lys Pro Met Lys Ser Val Leu Val Val Ala Leu Leu
1               5                   10                  15

Val Ile Phe Gln Val Cys Leu Cys Gln Asp Glu Val Thr Asp Asp Tyr
            20                  25                  30

Ile Gly Asp Asn Thr Thr Val Asp Tyr Thr Leu Phe Glu Ser Leu Cys
        35                  40                  45

Ser Lys Lys Asp Val Arg Asn Phe Lys Ala Trp Phe Leu Pro Ile Met
    50                  55                  60

Tyr Ser Ile Ile Cys Phe Val Gly Leu Leu Gly Asn Gly Leu Val Val
65                  70                  75                  80

Leu Thr Tyr Ile Tyr Phe Lys Arg Leu Lys Thr Met Thr Asp Thr Tyr
                85                  90                  95

Leu Leu Asn Leu Ala Val Ala Asp Ile Leu Phe Leu Leu Thr Leu Pro
            100                 105                 110

Phe Trp Ala Tyr Ser Ala Ala Lys Ser Trp Val Phe Gly Val His Phe
        115                 120                 125

Cys Lys Leu Ile Phe Ala Ile Tyr Lys Met Ser Phe Phe Ser Gly Met
    130                 135                 140

Leu Leu Leu Leu Cys Ile Ser Ile Asp Arg Tyr Val Ala Ile Val Gln
```

```
                145                 150                 155                 160
Ala Val Ser Ala His Arg His Arg Ala Arg Val Leu Leu Ile Ser Lys
                    165                 170                 175
Leu Ser Cys Val Gly Ser Ala Ile Leu Ala Thr Val Leu Ser Ile Pro
                180                 185                 190
Glu Leu Leu Tyr Ser Asp Leu Gln Arg Ser Ser Glu Gln Ala Met
            195                 200                 205
Arg Cys Ser Leu Ile Thr Glu His Val Glu Ala Phe Ile Thr Ile Gln
        210                 215                 220
Val Ala Gln Met Val Ile Gly Phe Leu Val Pro Leu Leu Ala Met Ser
225                 230                 235                 240
Phe Cys Tyr Leu Val Ile Ile Arg Thr Leu Leu Gln Ala Arg Asn Phe
                245                 250                 255
Glu Arg Asn Lys Ala Ile Lys Val Ile Ile Ala Val Val Val Val Phe
                260                 265                 270
Ile Val Phe Gln Leu Pro Tyr Asn Gly Val Val Leu Ala Gln Thr Val
            275                 280                 285
Ala Asn Phe Asn Ile Thr Ser Ser Thr Cys Glu Leu Ser Lys Gln Leu
        290                 295                 300
Asn Ile Ala Tyr Asp Val Thr Tyr Ser Leu Ala Cys Val Arg Cys Cys
305                 310                 315                 320
Val Asn Pro Phe Leu Tyr Ala Phe Ile Gly Val Lys Phe Arg Asn Asp
                325                 330                 335
Ile Phe Lys Leu Phe Lys Asp Leu Gly Cys Leu Ser Gln Glu Gln Leu
                340                 345                 350
Arg Gln Trp Ser Ser Cys Arg His Ile Arg Arg Ser Ser Met Ser Val
                355                 360                 365
Glu Ala Glu Thr Thr Thr Thr Phe Ser Pro
                370                 375

<210> SEQ ID NO 8
<211> LENGTH: 374
<212> TYPE: PRT
<213> ORGANISM: Homo sapiens
<220> FEATURE:
<223> OTHER INFORMATION: chemokine receptor CCR6

<400> SEQUENCE: 8

Met Ser Gly Glu Ser Met Asn Phe Ser Asp Val Phe Asp Ser Ser Glu
 1               5                  10                  15

Asp Tyr Phe Val Ser Val Asn Thr Ser Tyr Tyr Ser Val Asp Ser Glu
                20                  25                  30

Met Leu Leu Cys Ser Leu Gln Glu Val Arg Gln Phe Ser Arg Leu Phe
            35                  40                  45

Val Pro Ile Ala Tyr Ser Leu Ile Cys Val Phe Gly Leu Leu Gly Asn
        50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
```

-continued

```
            130                 135                 140
Ile Ala Ile Val Gln Ala Thr Lys Ser Phe Arg Leu Arg Ser Arg Thr
145                 150                 155                 160
Leu Pro Arg Thr Lys Ile Ile Cys Leu Val Val Trp Gly Leu Ser Val
                165                 170                 175
Ile Ile Ser Ser Ser Thr Phe Val Phe Asn Gln Lys Tyr Asn Thr Gln
                180                 185                 190
Gly Ser Asp Val Cys Glu Pro Lys Tyr Gln Thr Val Ser Glu Pro Ile
                195                 200                 205
Arg Trp Lys Leu Leu Met Leu Gly Leu Glu Leu Leu Phe Gly Phe Phe
210                 215                 220
Ile Pro Leu Met Phe Met Ile Phe Cys Tyr Thr Phe Ile Val Lys Thr
225                 230                 235                 240
Leu Val Gln Ala Gln Asn Ser Lys Arg His Lys Ala Ile Arg Val Ile
                245                 250                 255
Ile Ala Val Val Leu Val Phe Leu Ala Cys Gln Ile Pro His Asn Met
                260                 265                 270
Val Leu Leu Val Thr Ala Ala Asn Leu Gly Lys Met Asn Arg Ser Cys
                275                 280                 285
Gln Ser Glu Lys Leu Ile Gly Tyr Thr Lys Thr Val Thr Glu Val Leu
290                 295                 300
Ala Phe Leu His Cys Cys Leu Asn Pro Val Leu Tyr Ala Phe Ile Gly
305                 310                 315                 320
Gln Lys Phe Arg Asn Tyr Phe Leu Lys Ile Leu Lys Asp Leu Trp Cys
                325                 330                 335
Val Arg Arg Lys Tyr Lys Ser Ser Gly Phe Ser Cys Ala Gly Arg Tyr
                340                 345                 350
Ser Glu Asn Ile Ser Arg Gln Thr Ser Glu Thr Ala Asp Asn Asp Asn
                355                 360                 365
Ala Ser Ser Phe Thr Met
                370

<210> SEQ ID NO 9
<211> LENGTH: 342
<212> TYPE: PRT
<213> ORGANISM: Homo sapiens
<220> FEATURE:
<223> OTHER INFORMATION: chemokine receptor STRL33

<400> SEQUENCE: 9

Met Ala Glu His Asp Tyr His Glu Asp Tyr Gly Phe Ser Ser Phe Asn
1                 5                   10                  15
Asp Ser Ser Gln Glu Glu His Gln Asp Phe Leu Gln Phe Ser Lys Val
                20                  25                  30
Phe Leu Pro Cys Met Tyr Leu Val Val Phe Val Cys Gly Leu Val Gly
                35                  40                  45
Asn Ser Leu Val Leu Val Ile Ser Ile Phe Tyr His Lys Leu Gln Ser
        50                  55                  60
Leu Thr Asp Val Phe Leu Val Asn Leu Pro Leu Ala Asp Leu Val Phe
65                  70                  75                  80
Val Cys Thr Leu Pro Phe Trp Ala Tyr Ala Gly Ile His Glu Trp Val
                85                  90                  95
Phe Gly Gln Val Met Cys Lys Ser Leu Leu Gly Ile Tyr Thr Ile Asn
                100                 105                 110
Phe Tyr Thr Ser Met Leu Ile Leu Thr Cys Ile Thr Val Asp Arg Phe
```

```
               115                 120                 125
Ile Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
            340

<210> SEQ ID NO 10
<211> LENGTH: 740
<212> TYPE: DNA
<213> ORGANISM: Homo sapiens
<220> FEATURE:
<223> OTHER INFORMATION: DNA sequence 5' to the translation start site
                        of the CCX CKR gene

<400> SEQUENCE: 10
atgcagcatc tcgtttataa aaggcaacta gtgaaattta gtgcaaatgc tgagagaatt      60
tatttaactt atttaaatta aatttataaa taacatcaaa ataaaaaata aatttaatttt    120 aaataaacca gtaatttgc tattttcgtt tttattcaat tgttgtaga tatactttta      180 cgattcacaa aattatgtat gtaaagatta taacactatt tattcttttt agttaaaatc    240
taattaaatt ttcatatttt aaaaatcatt tttacataaa agtcttcact tttatttagg    300
atttaatgat taagaaaatt ctccagggca ttatgtttat tgtcctgttc aaatccaagc    360
tctttcacac agaattgtac aagcaaagtt tgagtaacta atcttggggt catattccaa    420
tgtggctccc attaaagcat tcaaagagt gctagattca ggctcacata tgttacagca     480
acaggctata ctctagggaa agaacaaaac agcttgatag aaactgtgtg cttttaagca    540
tatttagaca aatatctatc ctgtattctc tttgccatct agattggagc catggctttg    600
gaacagaacc gtcaacagat tattattatg aggagaagtg aaatgaatgg cctgatgact    660
acagtcagta tgaactgatc tgttcagaga agagacagag gatatgcaca gggttgctcc    720
```

-continued

```
ctgtattgct caccatagag                                               740
```

```
<210> SEQ ID NO 11
<211> LENGTH: 347
<212> TYPE: DNA
<213> ORGANISM: Homo sapiens
<220> FEATURE:
<223> OTHER INFORMATION: positions 1-347 of CXC CKR

<400> SEQUENCE: 11
atggctttgg aacagaacca gtcaacagat tattattatg aggaaaatga aatgaatggc    60
acttatgact acagtcaata tgaactgatc tgtatcaaag aagatgtcag agaatttgca   120
aaagttttcc tccctgtatt cctcacaata gttttcgtca ttggacttgc aggcaattcc   180
atggtagtgg caatttatgc ctattacaag aaacagagaa ccaaaacaga tgtgtacatc   240
ctgaatttgg ctgtagcaga tttactcctt ctattcactc tgccttttg gctgttaat    300 gcagttcatg ggtgggtttt agggaaaata atgtgcaaaa taacttc                347
```

```
<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence:peptide
      translation of non-coding region of SEQ ID NO:1

<400> SEQUENCE: 12

Asn Cys Ser Ala Phe Cys Leu Asp Thr Tyr Glu
  1               5                  10
```

```
<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:peptide
      translation of non-coding region of SEQ ID NO:1

<400> SEQUENCE: 13

Cys Phe Pro Leu Lys
  1               5
```

```
<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence:peptide
      translation of non-coding region of SEQ ID NO:1

<400> SEQUENCE: 14

Asn Ile Cys Leu Ile Leu Lys Lys Lys Lys Lys
  1               5                  10
```

CHEMOKINE RECEPTOR

CROSS-REFERENCE TO RELATED APPLICATIONS

This application is a continuation of U.S. patent application Ser. No. 09/721,495, filed Nov. 21, 2000, now U.S. Pat. No. 6,835,547, which is a continuation of U.S. patent application Ser. No. 09/686,019, filed Oct. 10, 2000, now abandoned, which claims benefit of U.S. Provisional Patent Application 60/159,015, filed Oct. 12, 1999, and U.S. Provisional Patent Application No. 60/159,210, filed Oct. 13, 1999, and U.S. Provisional Patent Application No. 60/172,979, filed December 20, 1999, and U.S. Provisional Patent Application 60/173,388, filed Dec. 28, 1999, and U.S. Provisional Patent Application 60/186,626, filed Mar. 3, 2000. The disclosure of each of the aforementioned applications is expressly incorporated herein by reference, in its entirety and for all purposes.

FIELD OF THE INVENTION

The invention relates to a human chemokine receptor, and to compositions and methods useful for diagnosing and treating physiologic and pathologic conditions mediated by the receptor and its ligand. The invention finds application in the biomedical sciences.

BACKGROUND OF THE INVENTION

Chemokines are a class of cytokines that play important roles in inflammatory responses, leukocyte trafficking, angiogenesis, and other biological processes related to the migration and activation of cells. As mediators of chemotaxis and inflammation, chemokines play roles in pathological conditions. For example, the concentration of the chemokine MCP-1 is higher in the synovial fluid of patients suffering from rheumatoid arthritis than that of patients suffering from other arthritic diseases.

Known chemokines are typically assigned to one of four subfamilies based on the arrangement of cysteine motifs. In the so-called alpha-chemokines, for example, the first two of four cysteines (starting from the amino terminus) are separated by an intervening amino acid (i.e., having the motif C—X—C). The beta-chemokines are characterized by the absence of an intervening amino acid between first two cysteines (i.e., comprising the motif C—C). The smaller gamma- and delta-chemokine families are characterized by a single C residue (gamma) or a pair of cysteines separated by three residues (delta; i.e., comprising the motif $CX_3C$). For a recent review on chemokines, see Ward et al., 1998, *Immunity* 9:1–11 and Baggiolini et al., 1998, *Nature* 392: 565–568, and the references cited therein.

Chemokine activity may be mediated by receptors. For example, several seven-transmembrane-domain G protein-coupled receptors for C—C chemokines have been cloned: a C—C chemokine receptor-1 which recognizes MIP-1α, RANTES, MCP-2, MCP-3, and MIP-5 (Neote et al., 1993, *Cell*, 72:415–415); CCR2 which is a receptor for MCP1, 2, 3 and 4 or 5; CCR3 which is a receptor for RANTES, MCP-2, 3, 4, MIP-5 and eotaxin; CCR5 which is a receptor for MIP-1α, MIP-1β and RANTES; CCR4 which is a receptor for MDC or TARC; CCR6 which is a receptor for LARC; and CCR7 which is a receptor for SLC and ELC (MIP-3β; reviewed in Sallusto et al., 1998, *Immunol. Today* 19:568 and Ward et al., 1998, *Immunity* 9:1–11).

Due to the importance of chemokines and their receptors as mediators of chemotaxis and inflammation, a need exists for the identification, isolation, and characterization of members of the chemokine receptor family to facilitate modulation of inflammatory and immune responses.

SUMMARY OF THE INVENTION

In one aspect, the invention provides a new chemokine receptor, CCX CKR. In one embodiment, the invention provides an isolated, substantially pure, or recombinant CCX CKR polypeptide, or immunogenic fragment thereof. In one embodiment the polypeptide has the amino acid sequence identical to SEQ ID NO:2. In another embodiment, the polypeptide with an amino acid sequence that differs from SEQ ID NO:2 by conservative mutations, which is at least 60%, 80%, or 90% identical to SEQ ID NO:2, and/or that is immunologically cross-reactive with the full-length polypeptide encoded by SEQ ID NO:2. In one embodiment, the polypeptide of the invention is a fusion protein. In some embodiments, the polypeptide of the invention has an activity of the CCX CKR, such as binding to a chemokine (e.g., ELC, SLC, TECK, BLC or vMIPII). In one embodiment, the polypeptide binds ELC, SLC, and TECK with high affinity.

In a related aspect, the invention provides an isolated polynucleotide that encodes, or is complementary to a sequence that encodes, the CCX CKR polypeptide. In some embodiments the polynucleotide has at least 10, 15, 25, 50 or 100 contiguous bases identical or exactly complementary to SEQ ID NO:1. In various embodiments, the polynucleotide is the full-length sequence of SEQ ID NO:1, encodes a CCX CKR polypeptide of the invention (e.g., having the sequence of SEQ ID:2 or a fragment thereof), or selectively hybridizes under high stringent hybridization conditions to a polynucleotide sequence of SEQ ID NO:1. The polynucleotide of the invention may be operably linked to a promoter. The invention provides recombinant vector (e.g., an expression vector) expressing the CCX CKR polypeptides of the invention. In one aspect, the invention provides a polynucleotide having sequence encoding a polypeptide that has an activity (e.g., a chemokine binding activity) of a CCX CKR polypeptide and which is (a) a polynucleotide having the sequence of SEQ ID NO:1 or SEQ ID NO 3; or (b) a polynucleotide which hybridizes under stringent conditions to (a); or (c) a polynucleotide sequence which is degenerate as a result of the genetic code to the sequences defined in (a) or (b).

The invention further provides a cell (e.g., a bacterial, eukaryotic, mammalian, or human cell) containing a recombinant CCX CKR polynucleotide of the invention, and provides a method for producing an CCX CKR protein, peptide, or fusion protein by culturing a cell containing the recombinant CCX CKR polynucleotide under conditions in which the polypeptide is expressed.

In another embodiment, the invention provides an antibody, or antibody fragment, or binding fragment (e.g., produced by phage display) that specifically binds to the CCX CKR polypeptide of the invention. The antibody may be monoclonal and may bind with an affinity of at least about $10^8$ $M^{-1}$. The invention also provides an isolated cell or a hybridoma capable of secreting the antibody. The antibody may be human or humanized.

In one aspect the invention provides a method of detecting an CCX CKR gene product in a sample by (a) contacting the sample with a probe that specifically binds the gene product, wherein the probe and the gene product form a complex, and detecting the formation of the complex; or (b) specifically amplifying the gene product in the biological sample, wherein said gene product is a polynucleotide, and detecting the formation of the complex or presence of the amplification product; wherein the formation of the complex or presence of the amplification product is correlated with the presence of the CCX CKR gene product in the biological sample. In one embodiment the gene product is a polypeptide and probe is an antibody. In a different embodiment, the gene product is an RNA and the probe is a polynucleotide.

The invention also provides a method for determining whether a compound does or does not interact directly with the CCX CKR polypeptide, by contacting a chemokine and the CCX CKR polypeptide or ligand binding fragment thereof, adding a test compound, and measuring any decrease in the binding of the chemokine. In various embodiments, the chemokine is ELC, SLC, TECK, BLC, mCTACK, mMIP-1γ or vMIPII or another naturally occurring ligand bound by the CCX CKR. In some embodiments, the chemokine is radiolabeled. Thus, in one aspect, the invention provides a method for identifying a modulator of the binding of CCX CKR to a chemokine by (a) contacting a polypeptide of encoding CCX CKR and the chemokine in the presence of a test compound, and (b) comparing the level of binding of the chemokine and the polypeptide in (a) with the level of binding in the absence of the test compound, wherein a decrease in binding indicates that the test compound is an inhibitor of binding and an increase in binding indicates that the test compound is an enhancer of binding. In one embodiment, the chemokine is ELC, SLC, TECK, BLC, mCTACK, mMIP-1γ or vMIPII. In an embodiment, the CCX CKR polypeptide is expressed by a cell.

In a related aspect, the invention provides a method of identifying a modulator of CCX CKR activity by contacting a cell expressing a recombinant CCX CKR polypeptide and a test compound and assaying for a biological effect that occurs in the presence but not absence of the test compound, wherein a test compound that induces a biological effect is identified as a modulator of CCX CKR activity. In one embodiment, the biological effect assayed for is receptor internalization. In some embodiments, the method also includes the step of contacting the cell with a chemokine that binds the receptor (e.g., ELC, SLC, TECK, BLC, mCTACK, mMIP-1γ or vMIPII) during the assay.

In another related aspect, the invention provides a process for making a pharmaceutical composition by formulating a modulator of CCX CKR activity (e.g., binding) for pharmaceutical use.

The invention also provides a method for identifying compounds which will be useful for the treatment of CCX CKR-mediated diseases and conditions, by determining whether the compound interacts with the CCX CKR.

In another aspect, the invention provides a method of treating an CCX CKR-mediated condition in a mammal by reducing or increasing the activity or expression of CCX CKR in a cell or tissue in the mammal or administering a modulator of CCX CKR function to the mammal. In various embodiments, the modulator of CCX CKR function is an inhibitor of binding of a chemokine (e.g., ELC) to CCX CKR or an enhancer of binding of a chemokine (e.g., ELC) to CCX CKR. In one embodiment, the invention provides a method of treating a CCX CKR-mediated condition or disease in a subject in need of such treatment by administering an effective amount of a compound that inhibits the binding of the CCX CKR and a chemokine. In various embodiments, the CCX CKR-mediated condition or disease is an inflammatory or allergic disease, an autoimmune disease, graft rejection, cancers, neoplastic diseases, retinopathy, macular degeneration, an infectious disease, or an immunosuppressive disease.

BRIEF DESCRIPTION OF THE FIGURES

FIG. 1 shows the nucleotide sequence for a human CCX CKR (SEQ. ID NO:1) and the predicted amino acid sequence of the human CCX CKR polypeptide (SEQ. ID NO:2).

FIG. 2 shows the CCX CKR sequence aligned with those of other chemokine receptors, the expression pattern of CCX CKR RNA, and generation of a stable cell line expressing CCX CKR. FIG. 2A shows sequence homology of the CCX CKR coding region with other chemokine receptors. FIG. 2B shows cells and tissues expressing CCX CKR RNA, as analyzed by RT-PCR of cytoplasmic RNA from cultured primary cells and whole tissues from various organs as indicated.

FIG. 3 shows the identification of CCX CKR ligands by adhesion to stalkokines.

FIG. 4: Definition of CCX CKR protein binding activity, as indicated by using $^{125}$I-ELC against a comprehensive array of viral, human, and murine chemokines in binding competition. The percent inhibition of specific binding is shown as a bar graph to emphasize that chemokines can be classed in categories as potential "high" affinity (solid bars), potential "moderate to low" affinity (hatched bars), or "no" affinity (open bars). The results are means of three determinations, the SEM in all cases is ≦20%; error bars are omitted for clarity. Since intra-assay experimental error was ±~20%, determinations within this range to the left or right of the 0% meridian are not likely to be statistically significant.

FIG. 5 shows DNA sequence 5' to the translation start site of the CCX CKR gene, as determined from a genomic clone.

FIG. 6 shows ligand induced internalization of CCX CKR in 293 cells transfected with a receptor-Flag epitope fusion plasmid.

DETAILED DESCRIPTION

I. Definitions

Figure 2C:
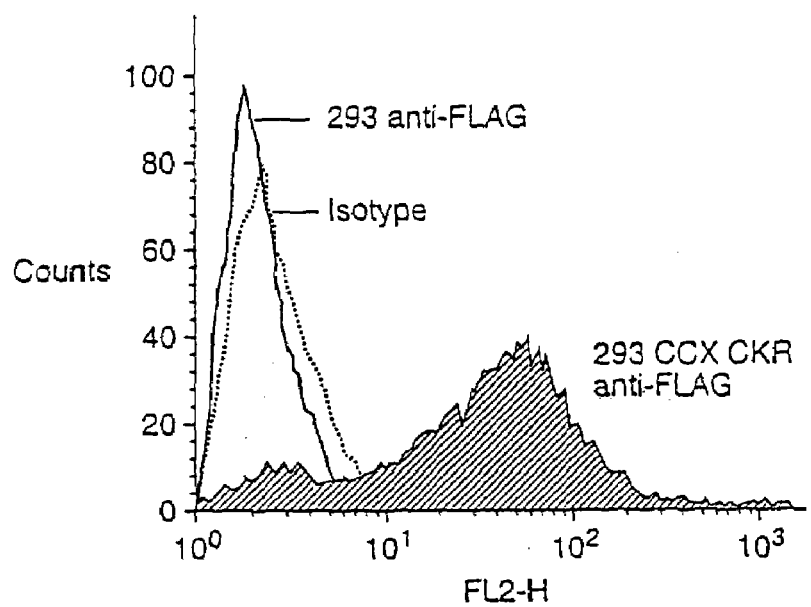
FIG. 2C shows a population of transfected HEK293 cells stably expressing CCX CKR protein containing an N-terminal Flag epitope, comparing intensity of anti-Flag mAb staining relative to wild type HEK293 cells.

The following definitions are provided to assist the reader in the practice of the invention.

The terms "allele" or "allelic sequence," as used herein, refer to a naturally-occurring alternative form of a gene encoding the CCX CKR polypeptide (i.e., a polynucleotide encoding an CCX CKR polypeptide). Alleles result from mutations (i.e., changes in the nucleic acid sequence), and sometimes produce altered and/or differently regulated mRNAs or polypeptides whose structure and/or function may or may not be altered. Common mutational changes that give rise to alleles are generally ascribed to natural deletions, additions, or substitutions of nucleotides that may or may not affect the encoded amino acids. Each of these types of changes may occur alone, in combination with the others, or one or more times within a given gene, chromosome or other cellular polynucleotide. Any given gene may have no, one or many allelic forms. As used herein, the term "allele" refers to either or both a gene or an mRNA transcribed from the gene.

As used herein, the term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an alpha-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "antisense sequences" refers to polynucleotides having sequence complementary to a RNA sequence. These terms specifically encompass nucleic acid sequences that bind to mRNA or portions thereof to block transcription of mRNA by ribosomes. Antisense methods are generally well known in the art (see, e.g., PCT publication WO 94/12633, and Nielsen et al., 1991, *Science* 254:1497; OLIGONUCLEOTIDES AND ANALOGUES, A PRACTICAL APPROACH, edited by F. Eckstein, IRL Press at Oxford University Press (1991); ANTISENSE RESEARCH AND APPLICATIONS (1993, CRC Press)).

The term "composition" as used herein is intended to encompass a product comprising the specified ingredients in the specified amounts, as well as any product which results, directly or indirectly, from combination of the specified ingredients in the specified amounts.

The term "conservative substitution," when describing a polypeptide, refers to a change in the amino acid composition of the polypeptide that does not substantially alter the activity of the polypeptide, i.e., substitution of amino acids with other amino acids having similar properties such that the substitutions of even critical amino acids does not substantially alter activity. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see also, Creighton, 1984, *Proteins*, W.H. Freeman and Company).

In addition to the above-defined conservative substitutions, other modification of amino acid residues can result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, e.g., often less than 5%, in an encoded sequence. Further, a conservatively modified variant can be made from a recombinant polypeptide by substituting a codon for an amino acid employed by the native or wild-type gene with a different codon for the same amino acid.

The terms "control elements" or "regulatory sequences" include enhancers, promoters, transcription terminators, origins of replication, chromosomal integration sequences, 5' and 3' untranslated regions, with which polypeptides or other biomolecules interact to carry out transcription and translation. For eukaryotic cells, the control sequences will include a promoter and preferably an enhancer, e.g., derived from immunoglobulin genes, SV40, cytomegalovirus, and a polyadenylation sequence, and may include splice donor and acceptor sequences. Depending on the vector system and host utilized, any number of suitable transcription and translation elements, including constitutive and inducible promoters, may be used. When referring to CCX CKR, a promoter other than that naturally associated with the CCX CKR coding sequence can be referred to as a "heterologous" promoter.

As used herein, a "derivatized" polynucleotide, oligonucleotide, or nucleic acid refers to oligo- and polynucleotides that comprise a derivatized substituent. In some embodiments, the substituent is substantially non-interfering with respect to hybridization to complementary polynucleotides. Derivatized oligo- or polynucleotides that have been modified with appended chemical substituents (e.g., by modification of an already synthesized oligo- or poly-nucleotide, or by incorporation of a modified base or backbone analog during synthesis) may be introduced into a metabolically active eukaryotic cell to hybridize with an CCX CKR DNA, RNA, or protein where they produce an alteration or chemical modification to a local DNA, RNA, or protein. Alternatively, the derivatized oligo or polynucleotides may interact with and alter CCX CKR polypeptides, or proteins that interact with CCX CKR DNA or CCX CKR gene products, or alter or modulate expression or function of CCX CKR DNA, RNA or protein. Illustrative attached chemical substituents include: europium (III) texaphyrin, cross-linking agents, psoralen, metal chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, base-modification agents, immunoglobulin chains, and oligonucleotides. Iron/ EDTA chelates are chemical substituents often used where local cleavage of a nucleic acid sequence is desired (Hertzberg et al., 1982, *J. Am. Chem. Soc.* 104: 313; Hertzberg and Dervan, 1984, *Biochemistry* 23: 3934; Taylor et al., 1984, *Tetrahedron* 40: 457; Dervan, 1986, *Science* 232: 464). Illustrative attachment chemistries include: direct linkage, e.g., via an appended reactive amino group (Corey and Schultz, 1988, *Science* 238: 1401, which is incorporated herein by reference) and other direct linkage chemistries, although streptavidin/biotin and digoxigenin/anti-digoxigenin antibody linkage methods can also be used. Methods for linking chemical substituents are provided in U.S. Pat. Nos. 5,135,720, 5,093,245, and 5,055,556, which are incorporated herein by reference. Other linkage chemistries may be used at the discretion of the practitioner.

As used herein, a "detectable label" has the ordinary meaning in the art and refers to an atom (e.g., radionuclide), molecule (e.g., fluorescein), or complex, that is or can be used to detect (e.g., due to a physical or chemical property), indicate the presence of a molecule or to enable binding of another molecule to which it is covalently bound or otherwise associated. The term "label" also refers to covalently bound or otherwise associated molecules (e.g., a biomolecule such as an enzyme) that act on a substrate to produce a detectable atom, molecule or complex. Detectable labels suitable for use in the present invention include any composition detectable by spectroscopic, photochemical, biochemical, immunochemical, electrical, optical, chemical means and the like.

The term "epitope" has its ordinary meaning of a site on an antigen recognized by an antibody. Epitopes are typically segments of amino acids which are a small portion of the whole polypeptide. Epitopes may be conformational (i.e., discontinuous). That is, they may be formed from amino acids encoded by noncontiguous parts of a primary sequence that have been juxtaposed by protein folding.

The term "fusion protein," refers to a composite polypeptide, i.e., a single contiguous amino acid sequence, made up of two (or more) distinct, heterologous polypeptides which are not normally fused together in a single amino acid sequence. Thus, a fusion protein may include a single amino acid sequence that contains two entirely distinct amino acid sequences or two similar or identical polypeptide sequences, provided that these sequences are not normally found together in the same configuration in a single amino acid sequence found in nature. Fusion proteins may generally be prepared using either recombinant nucleic acid methods, i.e., as a result of transcription and translation of a recombinant gene fusion product, which fusion comprises a segment encoding a polypeptide of the invention and a segment encoding a heterologous polypeptide, or by chemical synthesis methods well known in the art.

The term "gene product" refers to an RNA molecule transcribed from a gene, or a polypeptide encoded by the gene or translated from the RNA.

The term "high affinity" for an IgG antibody, as used herein, refers to an association constant (Ka) of at least about $10^6 M^{-1}$, preferably at least about $10^8 M^{-1}$, more preferably at least about $10^9 M^{-1}$ or greater, e.g., up to $10^{12} M^{-1}$ or greater. However, "high affinity" binding can vary for other antibody isotypes.

The terms "immunogen" and "immunogenic" have their ordinary meaning in the art, i.e., an immunogen is a molecule, such as a polypeptide or other antigen, that can elicit an adaptive immune response upon injection into a person or an animal.

The terms "modulator" and "modulation" of chemokine receptor activity, as used herein in its various forms, is intended to encompass antagonism, agonism, partial antagonism and/or partial agonism of the activity associated with a particular chemokine receptor, preferably the CCX CKR receptor. In various embodiments, "modulators" may inhibit or stimulate CCX CKR expression or activity, The terms "nucleic acid" and "polynucleotide" are used interchangeably and refer to deoxyribonucleotides or ribonucleotides and polymers thereof in either single- or double-stranded form. Unless specifically limited, the disclosure of a polynucleotide sequence is also intended to refer to the complementary sequence. As used herein, the term "polynucleotide" includes oligonucleotides.

The terms "oligonucleotides" or "oligomers" refer to a nucleic acid sequence of approximately 7 nucleotides or greater, and as many as approximately 100 nucleotides, which can be used as a primer or probe. Oligonucleotides are often between about 10 and about 50 nucleotides in length, more often between about 12 and about 50 nucleotides, very often between about 15 and about 25 nucleotides.

The term "operably linked" refers to a functional relationship between two or more polynucleotide (e.g., DNA) segments: for example, a promoter or enhancer is operably linked to a coding sequence if it stimulates the transcription of the sequence in an appropriate host cell or other expression system. Generally, sequences that are operably linked are contiguous, and in the case of a signal sequence both contiguous and in reading phase. However, enhancers need not be located in close proximity to the coding sequences whose transcription they enhance.

The terms "peptidomimetic" and "mimetic" refer to a synthetic chemical compound that has substantially the same structural and functional characteristics of the CCX CKR polypeptides of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, J. Adv. Drug Res. 15:29 (1986); Veber and Freidinger TINS p. 392 (1985); and Evans et al. J. Med. Chem. 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a CCX CKR, but have one or more peptide linkages optionally replaced by a linkage selected from the group consisting of, e.g., —CH2NH—, —CH2S—, —CH2-CH2-, —CH═CH— (cis and trans), —COCH2-, —CH(OH)CH2-, and —CH2SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of CCX CKR.

By "pharmaceutically acceptable" it is meant the carrier, diluent or excipient must be compatible with the other ingredients of the formulation and not deleterious to the recipient thereof.

The term "polypeptide" is used interchangeably herein with the term "protein," and refers to a polymer composed of amino acid residues linked by amide linkages, including synthetic, naturally-occurring and non-naturally occurring analogs thereof (amino acids and linkages). Peptides are examples of polypeptides.

As used herein, a "probe," when used in the context of polynucleotides and antibodies, refers to a molecule that specifically binds another molecule. One example of a probe is a "nucleic acid probe," which can be a DNA, RNA, or other polynucleotide. Where a specific sequence for a nucleic acid probe is given, it is understood that the complementary strand is also identified and included. The complementary strand will work equally well in situations where the target is a double-stranded nucleic acid that specifically binds (e.g., anneals or hybridizes) to a substantially complementary nucleic acid. Another example of a probe is an "antibody probe" that specifically binds to a corresponding antigen or epitope.

The term "recombinant" refers to a polynucleotide synthesized or otherwise manipulated in vitro (e.g., "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process is use of recombinant nucleic acid techniques, e.g., involving human intervention in the nucleotide sequence, typically selection or production. Alternatively, it can be a polynucleotide made by generating a sequence comprising fusion of two fragments which are not naturally contiguous to each other, but is meant to exclude products of nature. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

The phrase "selectively hybridizing to" refers to a polynucleotide probe that hybridizes, duplexes or binds to a particular target DNA or RNA sequence when the target sequences are present in a preparation of total cellular DNA or RNA.

The phrase "specifically immunoreactive," or "specifically binds" when referring to the interaction between an antibody and a protein or polypeptide, refers to an antibody that specifically recognizes and binds with relatively high affinity to the protein of interest, e.g., CCX CKR, such that this binding is determinative of the presence of the protein in a heterogeneous population of proteins and other biologics. Thus, under designated immunoassay conditions, the specified antibodies bind to a particular polypeptide and do not bind in a significant amount to other polypeptides present in the sample. A variety of immunoassay formats may be used to select antibodies specifically immunoreactive with a particular polypeptide. For example, solid-phase ELISA immunoassays are routinely used to select monoclonal antibodies specifically immunoreactive with a polypeptide. See, Harlow, 1988, ANTIBODIES, A LABORATORY MANUAL, Cold Spring Harbor Publications, New York (hereinafter, "Harlow"), for a description of immunoassay formats and conditions that can be used to determine specific immunoreactivity.

As used herein, the "substantially sequence identity," refers to two or more sequences or subsequences that have at least 60%, preferably 80%, most preferably 90%, 95%, 98%, or 99% nucleotide or amino acid residue identity, when compared and aligned for maximum correspondence, as measured using one of the following sequence comparison algorithms or by visual inspection. Two sequences (amino acid or nucleotide) can be compared over their full-length (e.g., the length of the shorter of the two, if they are of substantially different lengths) or over a subsequence such as at least about 50, about 100, about 200, about 500 or about 1000 contiguous nucleotides or at least about 10, about 20, about 30, about 50 or about 100 contiguous amino acid residues.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison Wis.), or by visual inspection (see generally Ausubel et al., Current Protocols In Molecular Biology, Greene Publishing and Wiley-Interscience, New York (supplemented through 1999). Each of these references and algorithms is incorporated by reference herein in its entirety. When using any of the aforementioned algorithms, the default parameters for "Window" length, gap penalty, etc., are used.

One example of algorithm that is suitable for determining percent sequence identity and sequence similarity is the BLAST algorithm, which is described in Altschul et al., J. Mol. Biol. 215:403–410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5 N=−4, and a comparison of both strands.

In addition to calculating percent sequence identity, the BLAST algorithm also performs a statistical analysis of the similarity between two sequences (see, e.g., Karlin & Altschul, Proc. Natl. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the first polypeptide (e.g., a polypeptide encoded by the first nucleic acid) is immunologically cross reactive with the second polypeptide (e.g., a polypeptide encoded by the second nucleic acid). Thus, a polypeptide is typically substantially identical to a second polypeptide, for example, where the two peptides differ only by conservative substitutions.

Another indication that two nucleic acid sequences are substantially identical is that the two molecules hybridize to each other under stringent conditions. Substantial identity exists when the segments will hybridize under stringent hybridization conditions to a strand, or its complement, typically using a sequence of at least about 50 contiguous nucleotides derived from the probe nucleotide sequences.

"Stringent hybridization conditions" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al.; supra; (1989) Molecular Cloning: A Laboratory Manual, 2nd Ed., Vols. 1–3, Cold Spring Harbor Laboratory). As indicated by standard references, a simple estimate of the Tm value may be calculated by the equation: Tm=81.5+0.41(% G+C), when a nucleic acid is in aqueous solution at 1 M NaCl (see e.g., Anderson and Young, "Quantitative Filter Hybridization" in Nucleic Acid Hybridization (1985)). Other references include more sophisticated computations which take structural as well as sequence characteristics into account for the calculation of Tm. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed.

The terms "substantially pure" or "isolated," when referring to proteins and polypeptides, e.g., CCX CKR, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition. When referring to polynucleotides, the terms "substantially pure" or "isolated" generally refer to the polynucleotide separated from contaminants with which it is generally associated, e.g., lipids, proteins and other polynucleotides. The substantially pure or isolated polynucleotides of the present invention will be greater than about 50% pure. Typically, these polynucleotides will be more than about 60% pure, more typically, from about 75% to about 90% pure and preferably from about 95% to about 98% pure.

The term "therapeutically effective amount" means the amount of the subject compound that will elicit the biological or medical response of a tissue, system, animal or human that is being sought by the researcher, veterinarian, medical doctor or other clinician.

As used herein, a receptor-mediated "biological effect" refers to a change in cell function or structure that results from the binding of the receptor to a naturally occuring ligand, (e.g., CCX CKR binding of ELC) and can include receptor internalization, receptor-mediated signaling (e.g., activation of a mammalian G protein, induction of rapid and transient increase in the concentration of cytosolic free calcium), a cellular response function (e.g., stimulation of chemotaxis or release of inflammatory mediators), and the like.

II. CCX CKR Polypeptides

The present invention provides isolated, substantially pure, or recombinant CCX CKR polypeptides and immunogenic fragments of mammalian CCX CKR polypeptides. In one embodiment, the CCX CKR polypeptide or fragment has an amino acid sequence identical to, or substantially identical to, the sequence set forth in SEQ ID NO:2 or a subsequence thereof.

A. CCX CKR Polypeptides and Variants

The invention provides substantially pure, isolated, or recombinant CCX CKR polypeptides. In some embodiments, the CCX CKR polypeptide has an amino acid sequence identical or substantially identical to the amino acid sequence shown in SEQ ID NO:2. In other embodiments, the CCX CKR polypeptides are variants and mutants characterized by conservative substitutions of amino acid residues of SEQ ID NO:2.

The polypeptide of the invention may be full-length (e.g., containing about 350 amino acids for the species shown in FIG. 1) or may encode a fragment of the full-length protein (e.g., comprising at least 20, at least 40, at least 60 or at least 100 residues of the CCX CKR polypeptides and variants of the invention. Also provided by the invention are CCX CKR polypeptides that are modified, relative to the amino acid sequence of SEQ ID NO:2, in some manner, e.g., truncated, mutated, derivatized, or fused to other sequences (e.g., to form a fusion protein). Some CCX CKR polypeptides comprise insertions, deletions or substitutions of amino acid residues relative to SEQ ID NO:2. For example, some conservative amino acid substitutions can be made, i.e., substitution of selected amino acids with different amino acids having similar structural characteristics, e.g., net charge, hydrophobicity, and the like.

Typically, the CCX CKR variants are structurally and functionally similar to the CCX CKR allele having the sequence of SEQ. ID. NO:2. Structural similarity is indicated by, e.g., substantial sequence identity (as defined above), or immunological cross-reactivity. Functional similarity is indicated by, e.g., a ligand-binding specificity similar to or the same as that of the naturally occurring CCX CKR allele CCX CKR allele having the sequence of SEQ. ID. NO:2 (e.g., binding ELC, SLC, and TECK with high affinity). In some embodiments, the CCX CKR polypeptide of the invention is a fusion protein or a fragment (e.g., a ligand binding fragment) of the full-length polypeptide encoded in SEQ. ID. NO:2. As used in this context, a "ligand binding fragment" of CCX CKR is a fragment of the receptor polypeptide that binds ELC (e.g., human or mouse ELC), SLC (human or mouse), or TECK (human or mouse) with high affinity (e.g., an apparent Ki or relational IC50 of less than about 15 nM) or moderate affinity (e.g., an apparent Ki or relational IC50 of at between about 15 and about 200 nM). Suitable assays for detecting binding are well known in the art. See, e.g., E. C Hulme "Receptor-Ligand Interactions" in A PRACTICAL APPROACH/THE PRACTICAL APPROACH SERIES (Series Eds D. Rickwood and B D Hames) IRL Press at Oxford University Press (1992), especially Ch. 6, Wang et al., "The se of the filtration technique in in vitro radioligand binding assays for membrane-bound and solubilized receptors," and Ch. 7, Hulme et al., "Centrifugation binding assays"; see also, Sissors et al., 1999, "A Homologous Receptor Binding Assay for HTS on FlashPlate plusNEN Life Science Products inc, Boston, Mass. 02118.

Figure 4A:
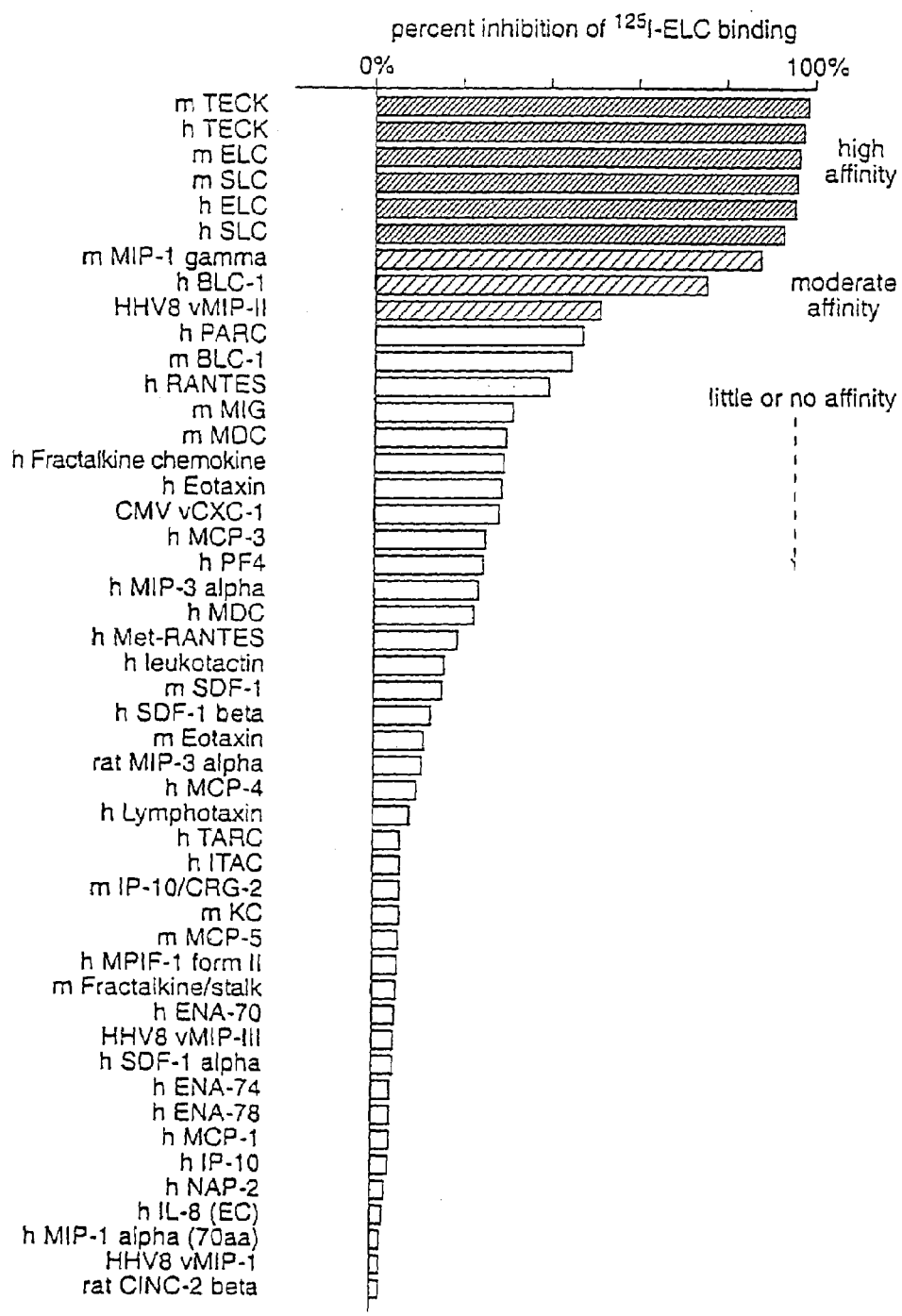
FIG. 4 shows the ligand binding fingerprint of CCX CKR.
FIG. 4B: Rank order of high affinity CCX CKR ligand binding. Multipoint determination reflecting the competition of unlabeled chemokines against $^{125}$I-ELC binding to CCX CKR. Representative result of equilibrium binding using cold (unlabeled) ELC, SLC, TECK, BLC, and vMIP-II, with calculated IC50s compared in the table at bottom.
Figure 4A:
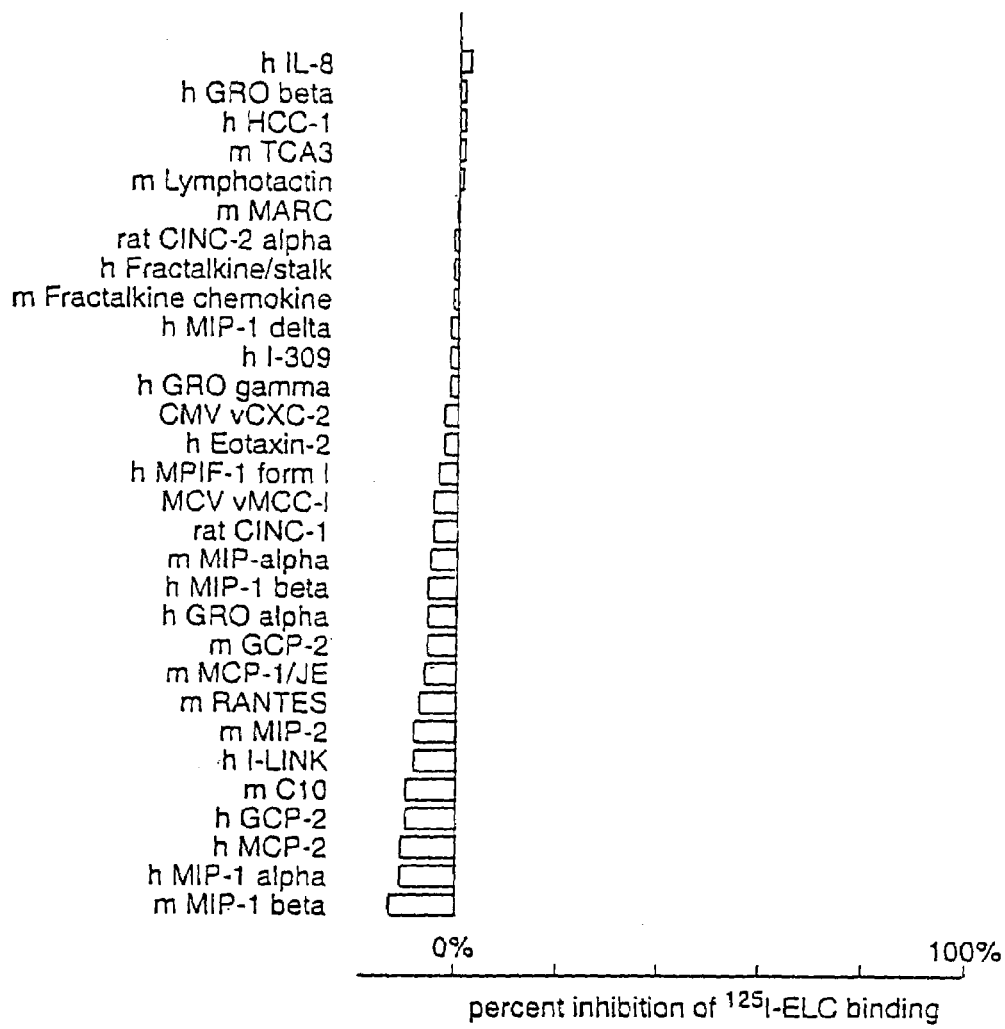

In one embodiment, binding is detected as described by Dairaghi et al., 1997, *J. Biol. Chem.* 272:28206–209 (incorporated by reference in its entirety for all purposes) substituting CCX CKR transfectants for the CCR3 transfectants). In one embodiment, binding is detected using the filter based technique described by Dairaghi et al., 1999, *J. Biol. Chem.* 274:2156 (incorporated by reference in its entirety for all purposes), e.g., as shown in FIG. 4. Briefly, this technology employs expanded, efficiency-maximized radioligand binding utilizing filtration protocols. In these assays, 1×10$^5$ CCXCKR-293 HEK cells are incubated with $^{125}$I-labeled ELC (MIP3beta) (final concentration of ~0.05 nM) in the presence of unlabeled chemokine for 3 h at 4° C. in 25 mM HEPES, 140 mM NaCl, 1 mM CaCl2, 5 mM MgCl2, and 0.2% bovine serum albumin, adjusted to pH 7.1. Reactions were aspirated onto PEI-treated GF/B glass filters using a cell harvester (Packard). Filters are washed twice (25 mM HEPES, 500 mM NaCl, 1 mM CaCl2 5 mM MgCl2, adjusted to pH 7.1) and scintillant (e.g., MicroScint 20; 50 μl) is added to dried filters and counted (e.g., using a Packard Topcount scintillation counter). The competition dose-response curves is analyzed by standard methods to determine IC50 values (e.g., using GraphPad Prism software (San Diego, Calif.)). Additionally, a Scatchard transformation can be used to estimate the receptor sites per cell (e.g., using WaveMetrics Igor software (Lake Oswego, Oreg.)).

As noted, binding assays are well known and it will be appreciated that binding can be detected using varying buffer conditions and incubation times and temperatures. For example, assays can be run at temperatures ranging from 37° to 4° C., preferably between about 4° C. and about 25° C., most preferably 4° C. or as well as incubation times from 1 hour to overnight (e.g., 3 hours). Buffer pH can range from 6.8 to 7.6, and NaCl concentrations may range from 0 to 160 mM (e.g., physiological buffer conditions). The percentage of BSA included can also vary from 0.1% to 0.5%. Exemplary conditions are incubation with 0.05 nM $^{125}$-labeled ELC in the presence of unlabeled chemokine for 3 h at 4° C. in 25 mM HEPES, 140 mM NaCl, 1 mM CaCl2, 5 mM MgCl2, and 0.2% bovine serum albumin, adjusted to pH 7.1. Other variations are known in the art.

As used herein, a chemokine specifically binds a CCX CKR polypeptide when it binds the receptor at least as well as a specified reference chemokine (e.g., ELC, SLC, TECK, mMIP-1γ, hBLC-1, mMIP-1γ, CTACK) known to bind wild-type CCX CKR with high or, alternatively, with moderate affinity.

In some embodiments, the CCX CKR polypeptide of the invention may be used as an immunogen (e.g., to produce anti-CCX CKR antibodies). Typically, the immunogenic CCX CKR fragments of the invention comprise at least about 6 contiguous residues of SEQ ID NO:2, more often at least about 8, about 10, or about 12, or about 16 contiguous residues.

The substantially pure, isolated or recombinant CCX CKR polypeptides of the present invention can also be characterized by their ability to bind antibodies that are specifically immunoreactive with a polypeptide having the sequence shown in SEQ ID NO:2. Specific immunoreactivity is usually characterized by a specific binding affinity of an antibody for its ligand (e.g., CCX CKR) of at least 10$^7$, 10$^8$, 10$^9$, or 10$^{10}$ M$^{-1}$.

For many applications, it will also be desirable to provide CCX CKR polypeptides of the invention as labeled entities, i.e., covalently attached or linked to a detectable label or group, or cross-linkable group, to facilitate identification, detection and quantification of the polypeptide in a given circumstance. These detectable groups can comprise a detectable polypeptide group, e.g., an assayable enzyme or antibody epitope. Alternatively, the detectable group can be selected from a variety of other detectable groups or labels, such as radiolabels (e.g., $^{125}$I, $^{32}$P, $^{35}$S) or a chemiluminescent or fluorescent group. Similarly, the detectable group can be a substrate, cofactor, inhibitor or affinity ligand.

In addition, a CCX CKR polypeptide can be modified by substituting one or more amino acid residues with a D-amino acid of the same type (e.g., D-lysine in place of L-lysine) to generate more stable peptides. Similarly, modification of the amino or carboxyl terminals can also be used to confer stabilizing properties upon the polypeptides of the invention, e.g., amidation of the carboxyl-terminus or acylation of the amino-terminus or pegylated derivatives.

B. Production and Isolation of CCX CKR Polypeptides

The CCX CKR polypeptides of the present invention can be prepared using recombinant or synthetic methods, or can be isolated from natural cellular sources.

Suitable recombinant techniques for expressing CCX CKR polypeptides from the CCX CKR polynucleotides are disclosed infra. See also, Sambrook et al., 1989, MOLECULAR CLONING: A LABORATORY MANUAL, (2nd ed.) Vols. 1–3, Cold Spring Harbor Laboratory, and in Ausubel, supra. Synthetic methods for synthesizing polypeptides such as CCX CKR polypeptides, variants, or fragments are described in Merrifield, 1963, *Amer. Chem. Soc.* 85:2149–2456, Atherton et al., 1989, SOLID PHASE PEPTIDE SYNTHESIS: A PRACTICAL APPROACH, IRL Press, and Merrifield, 1986, *Science* 232: 341–347.

Isolation and purification of the CCX CKR polypeptides of the present invention can be carried out by methods that are generally well known in the art. These methods include, but are not limited to, ion exchange, hydrophobic interaction, HPLC or affinity chromatography, to achieve the desired purity. In one embodiment, CCX CKR polypeptides are purified using immunoaffinity chromatography. For example, antibodies raised against a CCX CKR polypeptide or immunogenic fragment thereof (e.g., having a sequence or subsequence of SEQ ID NO:2) are coupled to a suitable solid support and contacted with a mixture of polypeptides containing the CCX CKR polypeptide (e.g., a homogenate of brain tissue) under conditions conducive to the association of this polypeptide with the antibody. Once the CCX CKR polypeptide is bound to the immobilized antibody, the solid support is washed to remove unbound material and/or nonspecifically bound polypeptides. The desired polypeptide can then be eluted from the solid support in substantially pure form by, e.g., a change in pH or salt concentration of the buffer.

C. Peptide Analogs and Peptide Mimetics of CCX CKR

Although primarily described in terms of "proteins" or "polypeptides," one of skill in the art will understand that structural analogs and derivatives of the above-described polypeptides, e.g., peptidomimetics, and the like can be used as substitutes for CCX CKR, e.g., as CCX CKR agonists, or, alternatively, as CCX CKR activity antagonists. Peptidomimetics, or peptide mimetics, are peptide analogs commonly used in the pharmaceutical industry as non-peptide drugs with properties (e.g., a biological activity) analogous to those of the template peptide (Fauchere, 1986, *Adv. Drug Res.* 15:29; Evans et al., 1987, *J. Med. Chem.* 30:1229). They are usually developed with the aid of computerized molecular modeling. Peptide mimetics that are structurally similar to therapeutically useful peptides can be used to produce an equivalent therapeutic effect. Peptide mimetics can have significant advantages over polypeptide embodiments, including, for example, more economical production and greater chemical stability.

III. CCX CKR Polynucleotides

In one aspect, the invention provides a polynucleotide having a sequence or subsequence of a mammalian (e.g., rat or human) CCX CKR gene or RNA. The polynucleotides of the invention (e.g., RNA, DNA, PNA or chimeras), may be single-stranded, double stranded, or a mixed hybrid. In one embodiment, the polynucleotide has a sequence of SEQ. ID NO: 1 (FIG. 1) or subsequences thereof (e.g., comprising at least 15, at least 25, at least 50, at least 100, at least 200, or at least 500 bases of the polynucleotides and variants of the invention). The invention also provides polynucleotides with substantial sequence identity to the CCX CKR polynucleotides disclosed herein. Thus, the invention provides naturally occurring alleles of mammalian (e.g., human) CCX CKR genes such as human allelic variants of the CCX CKR polynucleotides of SEQ ID NO:1.

As described infra, in some embodiments the polynucleotide of the invention encodes a polypeptide with substantial sequence similarity to SEQ. ID NO:2 (FIG. 1) or encodes a fragment of such a polypeptide (e.g., a fusion protein). Also contemplated are polynucleotides that, due to the degeneracy of the genetic code, are not substantially similar to SEQ ID NO:1, but encode the polypeptide of SEQ. ID NO:2 or a fragment thereof. In other embodiments, the invention provides CCX CKR polynucleotides that do not necessarily encode CCX CKR polypeptide but which are useful as e.g., probes, primers, antisense, triplex, or ribozyme reagents, and the like.

The invention also includes expression vectors, cell lines, and transgenic organisms comprising the CCX CKR polynucleotides. In some embodiments, the vectors, cells, and organisms of the invention are capable of expressing the encoded CCX CKR polypeptides.

Using the guidance of this disclosure, the CCX CKR polynucleotides of the invention can be produced by recombinant means. See, e.g., Sambrook et al., Berger and Kimmel, (1987) Methods In Enzymology, Vol. 152: Guide To Molecular Cloning Techniques, San Diego: Academic Press, Inc.; Ausubel et al., Current Protocols In Molecular Biology, Greene Publishing and Wiley-Interscience, New York (1999). Alternatively, CCX CKR polynucleotides or fragments can be chemically synthesized using routine methods well known in the art (see, e.g., Narang et al., 1979, *Meth. Enzymol.* 68:90; Brown et al., 1979, *Meth. Enzymol.* 68:109; Beaucage et al., 1981, *Tetra. Lett.*, 22:1859). In some embodiments, the CCX CKR polynucleotides of the invention contain non-naturally occurring bases, e.g., deoxyinosine (see, Batzer et al., 1991, *Nucleic Acid Res.* 19:5081; Ohtsuka et al., 1985, *J. Biol. Chem.* 260:2605–2608; Rossolini et al., 1994, *Mol. Cell. Probes* 8:91–98) or modified backbone residues or linkages.

A. Polynucleotides Encoding CCX CKR

In one aspect, the invention provides polynucleotides encoding CCX CKR polypeptides such as an CCX CKR polypeptide having the sequence of SEQ ID NO:2, a fragment thereof, a variant thereof (e.g., a conservative or allelic variant), or a CCX CKR fusion polypeptide. In one embodiment, the polynucleotide of the invention comprises the sequence of SEQ ID NO:1 or a fragment thereof. In another embodiment, the polynucleotide encodes a naturally occurring CCX CKR polypeptide or fragment, but has a sequence that differs from SEQ. ID NO:1 (e.g., as a result of the degeneracy of the genetic code). In some embodiments of the invention, the polynucleotide is other than the expressed sequence tags H67224, AI131555, AA215577, AW190975 or AI769466 or the polynucleotide encoding bovine PPR1 (Matsuoka et al., 1993, *Biochem Biophys Res Comm* 194: 540–11).

The polynucleotides of invention are useful for expression of CCX CKR polynucleotides (e.g., sense or antisense RNAs) and polypeptides. Methods for recombinant expression of polynucleotides and proteins are well known in the art. Typically, the CCX CKR polynucleotides of the invention are used in expression vectors for the preparation of CCX CKR polypeptides and polynucleotides. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells.

In one embodiment, DNA encoding an CCX CKR polypeptide of the present invention is inserted into DNA constructs capable of introduction into and expression in an in vitro host cell, such as a bacterial (e.g., *E. coli, Bacillus subtilus*), yeast (e.g., *Saccharomyces*), insect (e.g., *Spodoptera frugiperda*), or mammalian cell culture systems. Examples of mammalian cell culture systems useful for expression and production of the polypeptides of the present invention include human embryonic kidney line (293; Graham et al., 1977, *J. Gen. Virol*. 36:59); CHO (ATCC CCL 61 and CRL 9618); human cervical carcinoma cells (HeLa, ATCC CCL 2); and others known in the art. The use of mammalian tissue cell culture to express polypeptides is discussed generally in Winnacker, FROM GENES TO CLONES (VCH Publishers, N.Y., N.Y., 1987) and Ausubel, supra.

In some embodiments, promoters from mammalian genes or from mammalian viruses are used, e.g., for expression in mammalian cell lines. Suitable promoters can be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, and promoter-enhancer combinations known in the art.

CCX CKR polypeptides or fragments can also be expressed in transgenic animals (mouse, sheep, cow, etc.) and plants (tobacco, arabidopsis, etc.) using appropriate expression vectors which integrate into the host cell chromosome.

B. Polynucleotide or Oligonucleotide Probes and Primers

In one embodiment, the invention provides oligonucleotide or polynucleotide probes and/or primers for detecting or amplifying CCX CKR polynucleotides. In various embodiments, the polynucleotides (e.g., probes and primers) comprise at least 10 contiguous bases identical or exactly complementary to SEQ ID NO:1, usually at least 12 bases, typically at least 15 bases, generally at least 18 bases and often at least 25, at least 50, or at least 100 bases When the CCX CKR polynucleotides of the invention are used as probes or primers they are generally less that about 3000 bases in length; typically they contain between about 12 and about 100 contiguous nucleotides identical or exactly complementary to SEQ. ID NO:1, more often between about 12 and about 50 contiguous nucleotides, even more often between about 15 and about 25 contiguous nucleotides.

In some embodiments, the probes and primers are modified, e.g., by adding restriction sites to the probes or primers. In other embodiments, primers or probes of the invention comprise additional sequences, such as linkers. In still some other embodiments, primers or probes of the invention are modified with detectable labels. For example, the primers and probes are chemically modified, e.g., derivatized, incorporating modified nucleotide bases, or containing a ligand capable of being bound by an anti-ligand (e.g., biotin).

The CCX CKR probes and primers of the invention can be used for a number of purposes, e.g., for detecting or amplifying an CCX CKR polynucleotide in a biological sample, as discussed in more detail infra. For example, provided with the guidance herein, one of skill will be able to select primer pairs that specifically amplify all or a portion of the CCX CKR gene, mRNA, or cDNA in a sample. In a preferred embodiment, the primer pairs and amplification conditions are chosen to not amplify other chemokine receptor RNAs present in the sample, e.g., due to 3' mismatch between the CCX CKR primers and other gene sequences.

C. CCX CKR Inhibitors Polynucleotides

The invention provides inhibitory polynucleotides such as antisense, triplex, and ribozyme reagents that target or hybridize to CCX CKR polynucleotides.

1. Antisense Polynucleotides

In one aspect, the present invention provides antisense oligonucleotides and polynucleotides that can be used to inhibit expression of the CCX CKR gene. Some therapeutic methods of the invention, described in additional detail infra, involve the administration of an oligonucleotide that functions to inhibit or stimulate CCX CKR activity under in vivo physiological conditions, and is relatively stable under those conditions for a period of time sufficient for a therapeutic effect. Polynucleotides can be modified to impart such stability and to facilitate targeting delivery of the oligonucleotide to the desired tissue, organ, or cell.

The antisense polynucleotides of the invention comprise an antisense sequence of at least about 10 bases, typically at least 12 or 14, and up to about 3000 contiguous nucleotides that specifically hybridize to a sequence from mRNA encoding CCX CKR or mRNA transcribed from the CCX CKR gene. More often, the antisense polynucleotide of the invention is from about 12 to about 50 nucleotides in length or from about 15 to about 25 nucleotides in length. In general, the antisense polynucleotide should be long enough to form a stable duplex but short enough, depending on the mode of delivery, to administer in vivo, if desired. The minimum length of a polynucleotide required for specific hybridization to a target sequence depends on several factors, such as G/C content, positioning of mismatched bases (if any), degree of uniqueness of the sequence as compared to the population of target polynucleotides, and chemical nature of the polynucleotide (e.g., methylphosphonate backbone, peptide nucleic acid, phosphorothioate), among other factors.

Generally, to assure specific hybridization, the antisense sequence is substantially complementary to the target CCX CKR mRNA sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to CCX CKR RNA or its gene is retained as a functional property of the polynucleotide.

In one embodiment, the antisense sequence is complementary to relatively accessible sequences of the CCX CKR mRNA (e.g., relatively devoid of secondary structure). This can be determined by analyzing predicted RNA secondary structures using, for example, the MFOLD program (Genetics Computer Group, Madison Wis.) and testing in vitro or in vivo as is known in the art. Another useful method for identifying effective antisense compositions uses combinatorial arrays of oligonucleotides (see, e.g., Milner et al., 1997, *Nature Biotechnology* 15:537).

The invention also provides an antisense polynucleotide that has sequences in addition to the antisense sequence (i.e., in addition to anti-CCX CKR-sense sequence). In this case, the antisense sequence is contained within a polynucleotide of longer sequence. In another embodiment, the sequence of the polynucleotide consists essentially of, or is, the antisense sequence.

The antisense nucleic acids (DNA, RNA, modified, analogues, and the like) can be made using any suitable method for producing a nucleic acid, such as the chemical synthesis and recombinant methods disclosed herein. In one embodiment, for example, antisense RNA molecules of the invention may be prepared by de novo chemical synthesis or by cloning. For example, an antisense RNA that hybridizes to CCX CKR mRNA can be made by inserting (ligating) an CCX CKR DNA sequence (e.g., SEQ. ID No; 1, or fragment thereof) in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention. The antisense oligonucleotides of the invention can be used to inhibit CCX CKR activity in cell-free extracts, cells, and animals, including mammals and humans.

For general methods relating to antisense polynucleotides, see ANTISENSE RNA AND DNA, (1988), D. A. Melton, Ed., Cold Spring Harbor Laboratory, Cold Spring Harbor, N.Y.). See also, Dagle et al., 1991, *Nucleic Acids Research*, 19:1805. For a review of antisense therapy, see, e.g., Uhlmann et al., *Chem. Reviews*, 90:543–584 (1990).

2. Triplex Oligo- and Polynucleotides

The present invention provides oligo- and polynucleotides (e.g., DNA, RNA, PNA or the like) that bind to double-stranded or duplex CCX CKR nucleic acids (e.g., in a folded region of the CCX CKR RNA or in the CCX CKR gene), forming a triple helix-containing, or "triplex" nucleic acid. Triple helix formation results in inhibition of CCX CKR expression by, for example, preventing transcription of the CCX CKR gene, thus reducing or eliminating CCX CKR activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides of the invention are constructed using the base-pairing rules of triple helix formation (see, e.g., Cheng et al., 1988, *J. Biol. Chem.* 263: 15110; Ferrin and Camerini-Otero, 1991, *Science* 354:1494; Ramdas et al., 1989, *J. Biol. Chem.* 264:17395; Strobel et al., 1991, *Science* 254:1639; and Rigas et al., 1986, *Proc. Natl. Acad. Sci. U.S.A.* 83: 9591; each of which is incorporated herein by reference) and the CCX CKR mRNA and/or gene sequence. Typically, the triplex-forming oligonucleotides of the invention comprise a specific sequence of from about 10 to at least about 25 nucleotides or longer "complementary" to a specific sequence in the CCX CKR RNA or gene (i.e., large enough to form a stable triple helix, but small enough, depending on the mode of delivery, to administer in vivo, if desired). In this context, "complementary" means able to form a stable triple helix. In one embodiment, oligonucleotides are designed to bind specifically to the regulatory regions of the CCX CKR gene (e.g., the CCX CKR 5'-flanking sequence, promoters, and enhancers) or to the transcription initiation site, (e.g., between −10 and +10 from the transcription initiation site). For a review of recent therapeutic advances using triplex DNA, see Gee et al., in Huber and Carr, 1994, MOLECULAR AND IMMUNOLOGIC APPROACHES, Futura Publishing Co, Mt Kisco N.Y. and Rininsland et al., 1997, *Proc. Natl. Acad. Sci. USA* 94:5854, which are both incorporated herein by reference.

3. Ribozymes

The present invention also provides ribozymes useful for inhibition of CCX CKR activity. The ribozymes of the invention bind and specifically cleave and inactivate CCX CKR mRNA. Useful ribozymes can comprise 5'- and 3'-terminal sequences complementary to the CCX CKR mRNA and can be engineered by one of skill on the basis of the CCX CKR mRNA sequence disclosed herein (see PCT publication WO 93/23572, supra). Ribozymes of the invention include those having characteristics of group I intron ribozymes (Cech, 1995, *Biotechnology* 13:323) and others of hammerhead ribozymes (Edgington, 1992, *Biotechnology* 10:256).

Ribozymes of the invention include those having cleavage sites such as GUA, GUU and GUC. Other optimum cleavage sites for ribozyme-mediated inhibition of CCX CKR activity in accordance with the present invention include those described in PCT publications WO 94/02595 and WO 93/23569, both incorporated herein by reference. Short RNA oligonucleotides between 15 and 20 ribonucleotides in length corresponding to the region of the target CCX CKR gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assays, or by testing for in vitro ribozyme activity in accordance with standard procedures known in the art.

As described by Hu et al., PCT publication WO 94/03596, incorporated herein by reference, antisense and ribozyme functions can be combined in a single oligonucleotide. Moreover, ribozymes can comprise one or more modified nucleotides or modified linkages between nucleotides, as described above in conjunction with the description of illustrative antisense oligonucleotides of the invention.

In one embodiment, the ribozymes of the invention are generated in vitro and introduced into a cell or patient. In another embodiment, gene therapy methods are used for expression of ribozymes in a target cell ex vivo or in vivo.

4. Administration of Oligonucleotides

Typically, the therapeutic methods of the invention involve the administration of an oligonucleotide that functions to inhibit or stimulate CCX CKR activity under in vivo physiological conditions, and is relatively stable under those conditions for a period of time sufficient for a therapeutic effect. As noted above, modified nucleic acids may be useful in imparting such stability, as well as for targeting delivery of the oligonucleotide to the desired tissue, organ, or cell.

Oligo- and poly-nucleotides can be delivered directly as a drug in a suitable pharmaceutical formulation, or indirectly by means of introducing a nucleic acid into a cell, including liposomes, immunoliposomes, ballistics, direct uptake into cells, and the like as described herein. For treatment of disease, the oligonucleotides of the invention will be administered to a patient in a therapeutically effective amount. A therapeutically effective amount is an amount sufficient to ameliorate the symptoms of the disease or modulate CCX CKR activity in the target cell. Methods useful for delivery of oligonucleotides for therapeutic purposes are described in U.S. Pat. No. 5,272,065, incorporated herein by reference. Other details of administration of pharmaceutically active compounds are provided below. In another embodiment, oligo- and poly-nucleotides can be delivered using gene therapy and recombinant DNA expression plasmids of the invention.

D. Gene Therapy

Gene therapy refers to the introduction of an otherwise exogenous polynucleotide which produces a medically useful phenotypic effect upon the (typically) mammalian cell(s) into which it is transferred. In one aspect, the present invention provides gene therapy methods and compositions for treatment of CCX CKR-associated conditions. In illustrative embodiments, gene therapy involves introducing into a cell a vector that expresses an CCX CKR gene product (such as an CCX CKR protein substantially similar to the CCX CKR polypeptide having a sequence of SEQ. ID NO:2, e.g., to increase CCX CKR activity, or an inhibitory CCX CKR polypeptide to reduce activity), expresses a nucleic acid having an CCX CKR gene or mRNA sequence (such as an antisense RNA, e.g., to reduce CCX CKR activity), expresses a polypeptide or polynucleotide that otherwise affects expression of CCX CKR gene products (e.g., a ribozyme directed to CCX CKR mRNA to reduce CCX CKR activity), or replaces or disrupts an endogenous CCX CKR sequence (e.g., gene replacement and gene knockout, respectively). Numerous other embodiments will be evident to one of skill upon review of the disclosure herein.

Vectors useful in CCX CKR gene therapy can be viral or nonviral, and include those described supra in relation to the CCX CKR expression systems of the invention. It will be understood by those of skill in the art that gene therapy vectors may comprise promoters and other regulatory or processing sequences, such as are described in this disclosure. Usually the vector will comprise a promoter and, optionally, an enhancer (separate from any contained within the promoter sequences) that serve to drive transcription of an oligoribonucleotide, as well as other regulatory elements that provide for episomal maintenance or chromosomal integration and for high-level transcription, if desired. A plasmid useful for gene therapy can comprise other functional elements, such as selectable markers, identification regions, and other sequences. The additional sequences can have roles in conferring stability both outside and within a cell, targeting delivery of CCX CKR nucleotide sequences (sense or antisense) to a specified organ, tissue, or cell population, mediating entry into a cell, mediating entry into the nucleus of a cell and/or mediating integration within nuclear DNA. For example, aptamer-like DNA structures, or other protein binding moieties sites can be used to mediate binding of a vector to cell surface receptors or to serum proteins that bind to a receptor thereby increasing the efficiency of DNA transfer into the cell. Other DNA sites and structures can directly or indirectly bind to receptors in the nuclear membrane or to other proteins that go into the nucleus, thereby facilitating nuclear uptake of a vector. Other DNA sequences can directly or indirectly affect the efficiency of integration.

Suitable gene therapy vectors may, or may not, have an origin of replication. For example, it is useful to include an origin of replication in a vector for propagation of the vector prior to administration to a patient. However, the origin of replication can often be removed before administration if the vector is designed to integrate into host chromosomal DNA or bind to host mRNA or DNA.

As noted, the present invention also provides methods and reagents for gene replacement therapy (i.e., replacement by homologous recombination of an endogenous CCX CKR gene with a recombinant gene). Vectors specifically designed for integration by homologous recombination may be used. Important factors for optimizing homologous recombination include the degree of sequence identity and length of homology to chromosomal sequences. The specific sequence mediating homologous recombination is also important, because integration occurs much more easily in transcriptionally active DNA. Methods and materials for constructing homologous targeting constructs are described by e.g., Mansour et al., 1988, *Nature* 336: 348; Bradley et al., 1992, *Bio/Technology* 10: 534. See also, U.S. Pat. Nos. 5,627,059; 5,487,992; 5,631,153; and 5,464,764. In one embodiment, gene replacement therapy involves altering or replacing all or a portion of the regulatory sequences controlling expression of the CCX CKR gene that is to be regulated. For example, the CCX CKR promoter sequences (FIG. 5) may be disrupted (to decrease CCX CKR expression or to abolish a transcriptional control site) or an exogenous promoter (e.g., to increase CCX CKR expression) substituted.

The invention also provides methods and reagents for CCX CKR "gene knockout" (i.e., deletion or disruption by homologous recombination of an endogenous CCX CKR gene using a recombinantly produced vector). In gene knockout, the targeted sequences can be regulatory sequences (e.g., the CCX CKR promoter), or RNA or protein coding sequences. The use of homologous recombination to alter expression of endogenous genes is described in detail in U.S. Pat. No. 5,272,071, WO 91/09955, WO 93/09222, WO 96/29411, WO 95/31560, and WO 91/12650. See also, Moynahan et al., 1996, *Hum. Mol. Genet.* 5:875.

Gene therapy vectors may be introduced into cells or tissues in vivo, in vitro or ex vivo. For ex vivo therapy, vectors may be introduced into cells, e.g., stem cells, taken from the patient and clonally propagated for autologous transplant back into the same patient (see, e.g., U.S. Pat. Nos. 5,399,493 and 5,437,994, the disclosures of which are herein incorporated by reference).

IV. Antibodies

The present invention provides antibodies that are specifically immunoreactive with human CCX CKR polypeptide. Accordingly, the antibodies of the invention will specifically recognize and bind polypeptides which have an amino acid sequence identical, or substantially identical, to the amino acid sequence of SEQ ID NO:2, or an immunogenic fragment thereof. The antibodies of the invention usually exhibit a specific binding affinity for CCX CKR of at least about $10^7$, $10^8$, $10^9$, or $10^{10}$ $M^{-1}$.

The anti-CCX CKR antibodies of the invention have a variety of uses, e.g., isolation of CCX CKR polypeptides (e.g., by immunoaffinity chromatography), detection of CCX CKR polypeptides, and for inhibition of CCX CKR activity (e.g., in vivo or in vitro).

A. Production of Anti-CCX CKR Antibodies

Anti-CCX CKR antibodies of the present invention can be made by a variety of means well known to those of skill in the art, e.g., as described supra. As noted in Section I, supra, antibodies are broadly defined herein and specifically include fragments, chimeras and similar binding agents (e.g., the products of phage display technology), that specifically binds an CCX CKR polypeptide or epitope. However, the term "antibody" is not intended to refer to chemokines (e.g., ELC, SLC, TECK, BLC and vMIPII) that are bound by (i.e., ligands for) the CCX CKR.

Methods for production of polyclonal or monoclonal antibodies are well known in the art. See, e.g., Coligan, CURRENT PROTOCOLS IN IMMUNOLOGY, Wiley/Greene, NY (1991); Stites et al. (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler and Milstein, 1975, *Nature* 256:495–97; and Harlow and Lane. These techniques include antibody preparation by selection of antibodies from libraries of recombinant antibodies in phage or similar vectors. See, Huse et al., 1989, *Science* 246:1275–81; and Ward et al., 1989, *Nature* 341:544–46.

For production of polyclonal antibodies, an appropriate target immune system is selected, typically a mouse or rabbit, but also including goats, sheep, cows, chickens, guinea pigs, monkeys and rats. The immunoglobulins produced by the host can be precipitated, isolated and purified by routine methods, including affinity purification. Substantially monospecific antibody populations can be produced by chromatographic purification of polyclonal sera.

For monoclonal antibodies, appropriate animals will be selected and the desired immunization protocol followed The antibodies of the invention may be of any isotype, e.g., IgM, IgD, IgG, IgA, and IgE, with IgG, IgA and IgM most referred. Preferred monoclonal anti-CCX CKR antibodies neutralize (i.e., inhibit or block) one or more biological activities of CCX CKR. Such antibodies may be obtained by screening hybridoma supernatants for the desired inhibitory activity. Monoclonal antibodies with affinities of $10^8$ liters/mole, preferably $10^9$ to $10^{10}$ or stronger, can be produced by the methods described below. The production of non-human monoclonal antibodies, e.g., murine, lagomorpha, or equine, is well known and can be accomplished by, e.g., immunizing a host animal with a preparation containing CCX CKR or fragments thereof. Antibody-producing cells obtained from the immunized animals are immortalized and screened, or screened first for the production of antibody which binds to the CCX CKR polypeptide and then immortalized.

Some anti-CCX CKR monoclonal antibodies of the present invention are humanized, human or chimeric, in order to reduce their potential antigenicity, without reducing their affinity for their target. Humanized antibodies have been described in the art. See, e.g., Queen, et al., 1989, *Proc. Nat'l Acad. Sci. USA* 86:10029; U.S. Pat. Nos. 5,563,762; 5,693,761; 5,585,089 and 5,530,101. The human antibody sequences used for humanization can be the sequences of naturally occurring human antibodies or can be consensus sequences of several human antibodies. See Kettleborough et al., *Protein Engineering* 4:773 (1991); Kolbinger et al., *Protein Engineering* 6:971 (1993).

Humanized monoclonal antibodies against CCX CKR can also be produced using transgenic animals having elements of a human immune system (see, e.g., U.S. Pat. Nos. 5,569,825; 5,545,806; 5,693,762; 5,693,761; and 5,7124,350).

Useful anti-CCX CKR binding compositions can also be produced using phage display technology (see, e.g., Dower et al., WO 91/17271 and McCafferty et al., WO 92/01047). In these methods, libraries of phage are produced in which members display different antibodies on their outer surfaces. Antibodies are usually displayed as Fv or Fab fragments. Phage displaying antibodies with a desired specificity are selected by affinity enrichment to an CCX CKR polypeptide.

Once expressed, the whole antibodies, their dimers, individual light and heavy chains, or other immunoglobulin forms of the present invention can be purified according to standard procedures of the art, including ammonium sulfate precipitation, affinity chromatography, gel electrophoresis and the like (see generally PROTEIN PURIFICATION: PRINCIPLES AND PRACTICE 3RD EDITION (Springer-Verlag, N.Y., 1994)).

An antibody (e.g. an anti-CCX CKR antibody), is substantially pure when at least about 80%, more often at least about 90%, even more often at least about 95%, most often at least about 99% or more of the polypeptide molecules present in a preparation specifically bind the same antigen (e.g., CCX CKR polypeptide). For pharmaceutical uses, anti-CCX CKR immunoglobulins of at least about 90 to 95% homogeneity are preferred, and 98 to 99% or more homogeneity are most preferred.

B. Modification of CCX CKR Antibodies

The antibodies of the present invention can be used with or without modification. Frequently, the antibodies will be labeled by joining, either covalently or non-covalently, a substance which provides for a detectable signal. Such labels include those that are well known in the art, e.g., radioactive, fluorescent, or bioactive (e.g., enzymatic) labels. As labeled binding entities, the antibodies of the invention may be particularly useful in diagnostic applications.

Also encompassed by the invention are hybrid antibodies that share the specificity of antibodies against a CCX CKR polypeptide but are also capable of specific binding to a second moiety. In hybrid antibodies, one heavy and light chain pair is from one antibody and the other pair from an antibody raised against another epitope. This results in the property of multi-functional valency, i.e., ability to bind at least two different epitopes simultaneously. Such hybrids can be formed by fusion of hybridomas producing the respective component antibodies, or by recombinant techniques.

C. Selection of Non-Cross Reacting Antibodies

In some embodiments, an anti-CCX CKR monoclonal or polyclonal antiserum is produced that is specifically immunoreactive with CCX CKR and is selected to have low crossreactivity against other chemokine receptors, and any such crossreactivity is removed by immunoabsorption prior to use in the immunoassay. Methods for screening and characterizing monoclonal antibodies for specificity are well known in the art and are described generally in Harlow and Lane, supra.

In order to produce a polyclonal antisera (e.g., for use in an immunoassay), the protein of SEQ ID NO:2 a polyclonal antiserum is prepared using methods well known in the art such as those described supra. For example, recombinant protein may be produced in a mammalian cell line. An inbred strain of mice such as balb/c is immunized with the protein of SEQ ID NO:2 using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used as an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other human chemokine receptors (e.g., one or more of CCR1, CCR2, (CCR2A, CCR2B), CCR3, CCR4, CCR5, CCR6, CCR7, CCR8, CCR9A/B, CXCR1, CXCR2, CXCR3, CXCR4, CXCR5, $CX_3CR1$, and XCR1) or other G-protein coupled receptors (e.g., bovine PPR1) using a competitive binding immunoassay such as the one described in Harlow and Lane, supra, at pages 570–573. Immunoassays in the competitive binding format can be used for the crossreactivity determinations. For example, the protein of SEQ ID NO:2 can be immobilized to a solid support. Proteins added to the assay compete with the binding of the antisera to the immobilized antigen. The ability of the above proteins to compete with the binding of the antisera to the immobilized protein is compared to the protein of SEQ ID NO:2. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

V. Identification of CCX CKR Ligands

Chemokines to which CCX CKR binds were identified as described infra in Examples 4–6. The spectrum of ligands that bind to CCX CKR include ELC, SLC, CTACK, and TECK with high affinity, and BLC, mMIP-1γ, and vMIPII with lower affinity. The chemokines ELC (also called MIP-3beta) and SLC (also called 6Ckine), and their cognate receptor, CCR7, have profound effects on the regulation of dendritic cells (DC) and T cells. ELC and SLC have been shown to be major attractants of mature (though not immature) DC, and they have been suggested to control the migration of the newly postulated T central memory ($T_{CM}$) lymphocytes. Natural or targeted genetic deletions of ELC, SLC, or CCR7 result in marked deficiencies in DC, T and B cell trafficking, as well morphological disruption of secondary lymphoid organ architecture (Sallusto et al., 1999, *Nature* 401:708; Forster et al., 1999, *Cell* 99:23; Gunn et al., 1998, *Proc. Natl. Acad. Sci.* 95:258; Gunn et al., 1999, *J. Exp. Med.* 189:451; Yanagihara et al., 1998, *J. Immunol.* 161:3096; Yoshida et al. 1997, *J. Biol. Chem.* 272:13803; Yoshida et al., 1998, *J. Biol. Chem.* 273:7118). CCR7 is related to another chemokine receptor, CCR9 (formerly the orphan clone GPR9.6), shown to be a receptor for the CC chemokine TECK (Zabel et al., 1999, *J. Exp. Med.* 190: 1241; Zaballos et al., 1999, *J. Immunol.* 162:5671). The CCR9/TECK pairing has been reported to be important for the regulation of thymocytes, as well as lymphocytes with gut-targeted homing patterns (Youn et al., 1999, *Blood* 94:2533). To date, CCR9 has been the only reported TECK receptor and CCR7 the only credible receptor for ELC and SLC, despite contradictory reports (Jenh et al., 1999, *J. Immunol.* 162:3765; Soto et al., 1998, *Proc. Natl. Acad. Sci. USA* 95:8205) surrounding SLC binding.

VI. Screening and Identification of Modulators of CCX CKR Activity

The invention also provides assay methods which are capable of screening compounds that modulate the activity of the CCX CKR. Of particular interest are compounds that bind the CCX CKR, including compounds that compete for binding with a chemokine, ELC. This invention is particularly useful for screening compounds by using recombinant receptor in a variety of drug screening techniques. Thus, the present invention includes methods to evaluate putative specific agonists or antagonists of CCX CKR function. Accordingly, the present invention is directed to the use of these compounds in the preparation and execution of screening assays for compounds which modulate the activity of the CCX CKR chemokine receptor. For example, the compounds of this invention are useful for isolating receptor mutants, which are excellent screening tools for more potent compounds. Furthermore, the compounds of this invention are useful in establishing or determining the binding site of other compounds to the CCX CKR chemokine receptor, e.g., by competitive inhibition. The compounds of the instant invention are also useful for the evaluation of putative specific modulators of the CCX CKR chemokine receptor, relative to other chemokine receptors including CCR-1, CCR-2 (CCR2A, CCR2B), CCR-3, CCR-4, CCR-5 and CXCR-4.

A variety of assays can be used to evaluate the CCX CKR modulators, including CCX CKR binding assays, CCX CKR signaling assays, chemotaxis assays, second messenger levels, i.e., Ca++; cell proliferation; inositol phosphate pool changes; and other assays of cellular response.

One method of drug screening utilizes eukaryotic or prokaryotic host cells which are stably transformed with recombinant DNA molecules expressing the CCX CKR, e.g., the protein having the sequence of SEQ ID NO:2. Such cells, either in viable or fixed form, can be used for standard ligand/receptor binding assays (see e.g., Parce et al., 1989, *Science* 246: 243–247; and Owicki et al., 1990, *Proc. Nat'l Acad. Sci. USA* 87: 4007–4011, which describe sensitive methods to detect cellular responses). A test compound can be assayed for binding or for competition with another ligand for binding. Often, either the test compound or the "other ligand" is labeled. In various embodiments, test compounds are evaluated for competition with a chemokine or other ligand for binding to the CCX CKR or a ligand-binding fragment thereof. In some embodiments, the chemokine is ELC, SLC, TECK, BLC, CTACK, mMIP-1γ or vMIPII. In related embodiments, the chemokine is a chemokine other than ELC, SLC, TECK, BLC, CTACK, mMIP-1γ or vMIPII bound by the CCX CKR polypeptide with high or moderate affinity.

In a suitable assay, a CCX CKR protein (whether isolated or recombinant) is used which has at least one property, activity or functional characteristic of a human CCX CKR protein. The property can be a binding property (to, for example, a ligand or inhibitor) such as a binding profile (e.g., binding to ELC, SLC and TECK but not binding to chemokines bound with little or no affinity by the CCX CKR receptor polypeptide (e.g., of SEQ ID NO:2), e.g., binding to both TECK and ELC or SLC), a signaling activity (e.g., activation of a mammalian G protein, induction of rapid and transient increase in the concentration of cytosolic free calcium [Ca++]i), cellular response function (e.g., stimulation of chemotaxis or inflammatory mediator release by leukocytes), and the like.

In one embodiment, a composition containing a CCX CKR protein or variant thereof is maintained under conditions suitable for binding. The CCX CKR receptor is contacted with a putative agent (or a second composition containing at least one putative agent) to be test, and binding is detected or measured.

In one embodiment, the assay is a cell-based assay and cells are used which are stably or transiently transfected with a vector or expression cassette having a nucleic acid sequence which encodes the CCX CKR receptor. The cells are maintained under conditions appropriate for expression of the receptor and are contacted with a putative agent under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells.

Detection of binding or complex formation can be detected directly or indirectly. For example, the putative agent can be labeled with a suitable label (e.g., fluorescent label, chemiluminescent label, isotope label, enzyme label, and the like) and binding can be determined by detection of the label. Specific and/or competitive binding can be assessed by competition or displacement studies, using unlabeled agent or a ligand (e.g., ELC, SLC, TECK, BLC, mCTACK, mMIP-1γ or vMIPII) as a competitor.

In other embodiments, binding inhibition assays can be used to evaluate the present compounds. In these assays, the compounds are evaluated as inhibitors of ligand binding using, for example, ELC, SLC, TECK, BLC or vMIPII. In this embodiment, the CCX CKR receptor is contacted with a ligand such as ELC, SLC, TECK, BLC, mCTACK, mMIP-1γ or vMIPII, and a measure of ligand binding is made. The receptor is then contacted with a test agent in the presence of a ligand (e.g., ELC, SLC, TECK, BLC, mCTACK, mMIP-1γ or vMIPII) and a second measurement of binding is made. A reduction in the extent of ligand binding is indicative of inhibition of binding by the test agent. The binding inhibition assays can be carried out using whole cells which express CCX CKR, or a membrane fraction from cells which express CCX CKR.

The binding of a G protein-coupled receptor by, for example, an agonist, can result in a signaling event by the receptor. Accordingly, signaling assays can also be used to evaluate the compounds of the present invention and induction of signaling function by an agent can be monitored using any suitable method. For example, G protein activity, such as hydrolysis of GTP to GDP, or later signaling events triggered by receptor binding can be assayed by known methods (see, for example, PCT/US97/15915; Neote et al., 1993, Cell 72:415–25; Van Riper et al., 1993, J. Exp. Med., 177:851–56 and Dahinden et al., 1994, J. Exp. Med., 179: 751–56.

Chemotaxis assays can also be used to assess receptor function and evaluate the compounds provided herein. These assays are based on the functional migration of cells (e.g., cells expressing recombinant CCX CKR) in vitro or in vivo induced by an agent, and can be used to assess the binding and/or effect on chemotaxis of ligands, inhibitiors, or agonists. Suitable assays are described in PCT/US97/15915; Springer, et al., WO 94/20142; Berman et al., 1988. Immunol. Invest., 17:625–77 (1988); and Kavanaugh et al., 1991, J. Immunol., 146:4149–4156.

The test compounds, CCX CKR activity modulators or putative modulators and other compounds provided herein can also be evaluated using models of inflammation to assess the ability of the compound to exert an effect in vivo. Suitable models are described as follows: a sheep model for asthma (see, Weg et al., 1993, J. Exp. Med. 177:561); and a rat delayed-type hypersensitivity model (see Rand et al., 1996, Am. J. Pathol., 148:855–864). Another useful model for evaluating the instant compounds is the experimental autoimmune encephalomyelitis (EAE) model for multiple sclerosis, which probes chemokine receptor expression and function (see, Ransohoff et al., 1996, Cytokine Growth Factor Rev., 7:35–46, and Karpus et al., 1998, J. Immunol. 161:2667–2671).

In addition, leukocyte infiltration assays can also be used to evaluate a compound (see, Van Damme, et al., 1992, J. Exp. Med., 176:59–65; Zachariae et al., 1990, J. Exp. Med, 171:2177–2182; and Jose et al., 1994, J. Exp. Med., 179: 881–887).

Several methods of automating assays have been developed in recent years so as to permit screening of tens of thousands of compounds in a short period. See, e.g., Fodor et al., 1991, Science 251: 767–73, and other descriptions of chemical diversity libraries, which describe means for testing of binding affinity by a plurality of compounds. The development of suitable assays can be greatly facilitated by the availability of large amounts of purified CCX CKR and/or cells expressing recombinant CCX CKR, as provided by this invention.

In embodiments of the detection and screening methods of the invention, the chemokine and the CCX CKR polypeptide are of the same species. In related embodiments, the chemokine naturally binds the receptor.

Using the screening methods described in Example 7, exemplary "small molecule" modulators of CCX CKR binding to ELC were identified (see Table 1). These compounds, or structurally related compounds, are used as modulators (agonists or antagonists) of CCX CKR activity, in assays to identify other modulators and agents, to further characterize the CCX CKR, and for identification of structurally related modulators with greater or different activity.

TABLE 1

Exemplary Small Molecule Modulators of CCX CKR Function

Compound I
(antagonist)

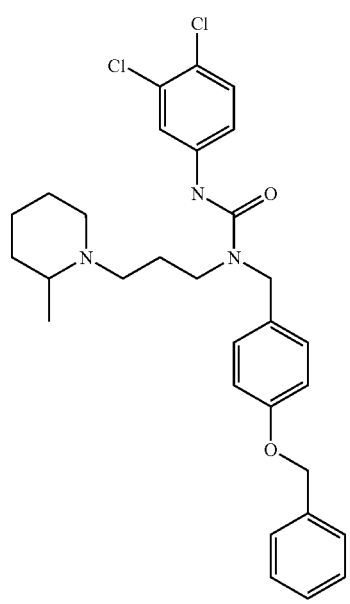

TABLE 1-continued

Exemplary Small Molecule Modulators of CCX CKR Function

Compound II
(antagonist)

Compound III
(agonist)

VII. Methods of Treating CCX CKR-Mediated Conditions or Diseases

In yet another aspect, the present invention provides methods of treating CCX CKR-mediated conditions or diseases by administering to a subject having such a disease or condition, a therapeutically effective amount of an modulator of CCX CKR function, i.e., agonists (stimulators) and antagonists (inhibitors) of CCX CKR function or gene expression. Such modulators include small molecules agonists and antagonists of CCX CKR function; polypeptide inhibitors (e.g., dominant-negative mutants); antisense, ribozyme and triplex polynucleotides; gene therapy (for inhibition, e.g., gene knockout, or overexpression), and the like.

Diseases and conditions associated with inflammation, infection and cancer can be treated with the present compounds and compositions. In one group of embodiments, diseases or conditions, including chronic diseases, of humans or other species can be treated with inhibitors of CCX CKR function. These diseases or conditions include: (1) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), multiple sclerosis, systemic lupus erythematosus, diabetes, glomerulonephritis, and the like, (3) graft rejection (including allograft rejection and graft-vs-host disease), and (4) other diseases in which undesired inflammatory responses are to be inhibited (e.g., atherosclerosis, myositis). In another group of embodiments, diseases or conditions are treated with agonists of CCX CKR function or reagents or methods for increasing CCX CKR expression. Examples of diseases to be treated with CCX CKR agonists include cancers, diseases in which angiogenesis or neovascularization play a role (neoplastic diseases, retinopathy and macular degeneration), infectious diseases and immunosuppressive diseases. CCX CKR gene products, agonists, and antagonists similarly find use is tissue and organ remodeling, repair, and regeneration.

For example, modulators of CCX CKR activity can inhibit the proliferation and differentiation of cells involved in an inflammatory response. The term "inflammation" has the normal meaning in the art refers to both acute responses (i.e., responses in which the inflammatory processes are active) and chronic responses (i.e., responses marked by slow progression and formation of new connective tissue). Acute and chronic inflammation can be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Assays for inflammation are well known in the art. The reagents provided by the present invention can be used to treat inflammatory conditions, both chronic and acute conditions, including inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from overproduction of cytokines (e.g., TNF or IL-1). Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

The methods and reagents of the invention may be used in treatment of animals such as mammals (e.g., humans, non-human primates, cows, sheep, goats, horses, dogs, cats, rabbits, rats, mice) or in animal or in vitro (e.g., cell-culture) models of human diseases.

VIII. Pharmaceutical Compositions

The present invention further provides therapeutic compositions comprising agonists, antagonists, or ligands of CCX CKR, and methods of treating physiologic or pathologic conditions mediated by CCX CKR.

CCX CKR polypeptides, fragments thereof, sense and antisense polypeptides, anti-CCX CKR antibodies or binding fragments thereof, and antagonists or agonists (e.g. small molecule modulators) of CCX CKR activity, can be directly administered under sterile conditions to the host to be treated. However, while it is possible for the active ingredient to be administered alone, it is often preferable to present it as a pharmaceutical formulation. Formulations typically comprise at least one active ingredient together with one or more acceptable carriers thereof. Each carrier should be both pharmaceutically and physiologically acceptable in the sense of being compatible with the other ingredients and not injurious to the patient. For example, the bioactive agent can be complexed with carrier proteins such as ovalbumin or serum albumin prior to their administration in order to enhance stability or pharmacological properties such as half-life. Furthermore, therapeutic formulations of this invention can be combined with or used in association with other chemotherapeutic or chemopreventive agents.

Therapeutic formulations can be prepared by any methods well known in the art of pharmacy. See, e.g., Gilman et al (eds.) (1990) Goodman and Gilman's: The Pharmacological Bases of Therapeutics (8th ed.) Pergamon Press; and (1990) Remington's Pharmaceutical Sciences (17th ed.) Mack Publishing Co., Easton, Pa; Avis et al (eds.) (1993) Pharmaceutical Dosage Forms: Parenteral Medications Dekker, N.Y.; Lieberman et al. (eds.) (1990) Pharmaceutical Dosage Forms: Tablets Dekker, N.Y.; and Lieberman et al (eds.) (1990) Pharmaceutical Dosage Forms: Disperse Systems Dekker, N.Y.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. As used herein, topical application is also meant to include the use of mouth washes and gargles.

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be about 0.005 to about 0.05, 0.05 to 0.5 or 0.5 to 5 mg/kg per day. For oral administration, the compositions are preferably provided in the form of tablets containing about 1 to 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention can be combined with other compounds having related utilities to prevent and treat inflammatory and immunoregulatory disorders and diseases, including asthma and allergic diseases as well as autoimmune pathologies such as rheumatoid arthritis and atherosclerosis, and those pathologies noted above.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists, (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as beta2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106, 203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) antidiabetic agents such as insulin, sulfonylureas, biguanides (metformin), alpha-glucosidase inhibitors (acarbose) and glitazones (troglitazone and pioglitazone); (l) preparations of interferon beta (interferon beta-1 alpha, interferon beta-1beta); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

IX. Detection and Quantification of CCX CKR Polynucleotides and Polypeptides

The present invention provides a number of methods for detection and quantification of CCX CKR polypeptides and polynucleotides in biological samples. In one embodiment, expression or over expression of the CCX CKR gene product (e.g., polypeptide or mRNA) is correlated with a disease or condition mediated by, or associated with the CCX CKR. It will be appreciated from the expression pattern of CCX CKR mRNA (see FIG. 2B) that detection of CCX CKR gene products is particularly useful for identifying cell state, e.g., to identify immature (in contrast to mature) dendritic cells as well as activated T cells.

The biological samples can include, but are not limited to, a blood sample, serum, cells (including whole cells, cell fractions, cell extracts, and cultured cells or cell lines), tissues (including tissues obtained by biopsy), body fluids (e.g., urine, sputum, amniotic fluid, synovial fluid), or from media (from cultured cells or cell lines), and the like. The methods of detecting or quantifying CCX CKR polynucleotides include, but are not limited to, amplification-based assays with or without signal amplification, hybridization based assays, and combination amplification-hybridization assays. For detecting and quantifying CCX CKR polypeptides, an exemplary method is an immunoassay that utilizes an antibody or other binding agents that specifically binds to an CCX CKR polypeptide or epitope.

A. Assays for CCX CKR Polynucleotides

1. Amplification-based Methods

The polymerase chain reaction (PCR), or its variations, is an exemplary amplification-based assay. Examples of techniques sufficient to direct persons of skill through in vitro amplification methods are found in PCR TECHNOLOGY: PRINCIPLES AND APPLICATIONS FOR DNA AMPLIFICATION, H. Erlich, Ed. Freeman Press, New York, N.Y. (1992); PCR PROTOCOLS: A GUIDE TO METHODS AND APPLICATIONS, eds. Innis, Gelfland, Snisky, and White, Academic Press, San Diego, Calif. (1990). Other suitable target amplification methods include the ligase chain reaction (LCR; e.g., Wu and Wallace, 1989, *Genomics* 4:560); strand displacement amplification (SDA; e.g., Walker et al., 1992, *Proc. Natl. Acad. Sci. U.S.A.* 89:392–396); the nucleic acid sequence based amplification (NASBA, Cangene, Mississauga, Ontario; e.g., Compton, 1991, *Nature* 350:91), and the like.

One useful variant of PCR is PCR ELISA (e.g., Boehringer Mannheim Cat. No. 1 636 111) in which digoxigenin-dUTP is incorporated into the PCR product. The PCR reaction mixture is denatured and hybridized with a biotin-labeled oligonucleotide designed to anneal to an internal sequence of the PCR product. The hybridization products are immobilized on streptavidin coated plates and detected using anti-digoxigenin antibodies.

2. Hybridization-based Methods

A variety of methods for specific DNA and RNA measurement using polynucleotide hybridization techniques are known to those of skill in the art (see Sambrook, supra). Hybridization based assays refer to assays in which a polynucleotide probe is hybridized to a target polynucleotide. Usually the polynucleotide hybridization probes of the invention are entirely or substantially identical to a contiguous sequence of the CCX CKR nucleic acid sequence. Preferably, polynucleotide probes are at least about 10 bases, often at least about 20 bases, and sometimes at least about 200 bases or more in length. Methods of selecting polynucleotide probe sequences for use in polynucleotide hybridization are discussed in Sambrook, supra.

Polynucleotide hybridization formats are known to those skilled in the art. In some formats, at least one of the target and probe is immobilized. The immobilized polynucleotide may be DNA, RNA, or another oligo- or poly-nucleotide, and may comprise natural or non-naturally occurring nucleotides, nucleotide analogs, or backbones. Such assays may be in any of several formats including: Southern, Northern, dot and slot blots, high-density polynucleotide or oligonucleotide arrays (e.g., GeneChips™ Affymetrix), dip sticks, pins, chips, or beads. All of these techniques are well known in the art and are the basis of many commercially available diagnostic kits. Hybridization techniques are generally described in Hames et al., ed., николеиc Acid Hybridization, A Practical Approach IRL Press, (1985); Gall and Pardue *Proc. Natl. Acad. Sci., U.S.A.*, 63: 378–383 (1969); and John et al., *Nature*, 223: 582–587 (1969).

In one embodiment, in situ hybridization is used to detect CCX CKR sequences in a sample. In situ hybridization assays are well known and are generally described in Angerer et al., Methods Enzymol., 152: 649–660 (1987) and Ausubel, supra.

B. CCX CKR Polypeptide Assays

In one embodiment, the CCX CKR polynucleotide is detected in a sample using an anti-CCX CKR antibody of the invention. A number of well established immunological binding assay are suitable for detecting and quantifying CCX CKR of the present invention. See, e.g., U.S. Pat. Nos. 4,366,241; 4,376,110; 4,517,288; and 4,837,168, and also Methods in Cell Biology Volume 37: Antibodies in Cell Biology, Asai, ed. Academic Press, Inc. New York (1993); Basic and Clinical Immunology 7th Edition, Stites & Terr, eds. (1991); Harlow, supra [e.g., Chapter 14], and Ausubel, supra, [e.g., Chapter 11], each of which is incorporated by reference in its entirety and for all purposes.

Immunoassays for detecting CCX CKR may be competitive or noncompetitive. Usually the CCX CKR gene product being assayed is detected directly or indirectly using a detectable label. The particular label or detectable group used in the assay is usually not a critical aspect of the invention, so long as it does not significantly interfere with the specific binding of the antibody or antibodies used in the assay. The label may be covalently attached to the capture agent (e.g., an anti-CCX CKR antibody), or may be attached to a third moiety, such as another antibody, that specifically binds to the CCX CKR polypeptide at a different epitope than recognized by the capture agent.

1. Non-Competitive Immunoassay

Noncompetitive immunoassays are assays in which the amount of captured analyte (here, the CCX CKR polypeptide) is directly measured. One such assay is a two-site, monoclonal-based immunoassay utilizing monoclonal antibodies reactive to two non-interfering epitopes on the captured analyte. See, e.g., Maddox et al., 1983, *J. Exp. Med.*, 158:1211 for background information. In such an assay, the amount of CCX CKR in the sample is directly measured. For example, using a so-called "sandwich" assay, the capture agent (here, the anti-CCX CKR antibodies) can be bound directly to a solid substrate where they are immobilized. These immobilized antibodies then capture polypeptide present in the test sample. CCX CKR thus immobilized is then bound by a labeling agent, such as a second CCX CKR antibody bearing a label. Alternatively, the second CCX CKR antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Immunoassay

In competitive assays, the amount of CCX CKR polypeptide present in the sample is measured indirectly by measuring the amount of an added (exogenous) CCX CKR displaced (or competed away) from a capture agent (e.g., anti-CCX CKR antibody) by the analyte present in the sample (e.g., CCX CKR polypeptide). In one competitive assay, a known amount of CCX CKR is added to the sample and the sample is then contacted with a capture agent (e.g., an anti-CCX CKR antibody) that specifically binds to CCX CKR. The amount of CCX CKR bound to the antibody is inversely proportional to the concentration of CCX CKR present in the sample.

Preferably, the antibody is immobilized on a solid substrate. The amount of CCX CKR bound to the antibody may be determined either by measuring the amount of CCX CKR present in an CCX CKR/antibody complex, or alternatively by measuring the amount of remaining uncomplexed CCX CKR. The amount of CCX CKR may be detected by providing a labeled CCX CKR molecule.

For example, using the hapten inhibition assay, the analyte (in this case CCX CKR) is immobilized on a solid substrate. A known amount of anti-CCX CKR antibody is added to the sample, and the sample is then contacted with the immobilized CCX CKR. In this case, the amount of anti-CCX CKR antibody bound to the immobilized CCX CKR is inversely proportional to the amount of CCX CKR present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Other Assays

In addition to the competitive and non-competitive CCX CKR polypeptide immunoassays, the present invention also provides other assays for detection and quantification of CCX CKR polypeptides. For example, Western blot (immunoblot) analysis can be used to detect and quantify the presence of CCX CKR in the sample. The technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the sample with the antibodies that specifically bind CCX CKR. The anti-CCX CKR antibodies specifically bind to CCX CKR on the solid support. These antibodies may be directly labeled or alternatively may be subsequently detected using labeled antibodies (e.g., labeled sheep anti-mouse antibodies) that specifically bind to the anti-CCX CKR.

Furthermore, assays such as liposome immunoassays (LIA) are also encompassed by the present invention. LIA utilizes liposomes that are designed to bind specific molecules (e.g., antibodies) and to release encapsulated reagents or markers. The released chemicals are then detected according to standard techniques (see, Monroe et al., 1986, *Amer. Clin. Prod. Rev.* 5:34–41).

In a different embodiment, the CCX CKR protein can be detected using detectably-labeled chemokine ligands that bind the receptor, e.g., labeled ELC, SLC, TECK, BLC, mCTACK, mMIP-1γ and vMIPII.

X. Kits

Reagents useful for the therapeutic and diagnostic (detection) methods of the invention are conveniently provided in kit form. Thus, the present invention encompasses kits that contain polypeptides, antibodies, and polynucleotides of the present invention.

In one embodiment, the kit comprises one or more of the following in a container: (1) CCX CKR polynucleotides (e.g., oligonucleotide primers or probes corresponding to the CCX CKR cDNA sequence and capable of amplifying the target polynucleotides); (2) anti-CCX CKR antibodies; (3) CCX CKR polypeptides or fragments, optionally coated on a solid surface (such as a slide, multiple well plate, or test tube) (4) a CCX CKR polynucleotide (e.g., for use as positive controls in assays), (5) and tubes. Instructions for carrying out the detection methods of the invention, and calibration curves can also be included.

XI. CHEMOKINE REFERENCES

Chemokines are well known in the art. Exemplary chemokines include those listed in FIG. 4(a) and homologs in other species (e.g., mammalian, mouse, rat rabbit, human, non-human primate, and the like. The following references describe certain cytokines. Additional references describing these and other chemokines known in the art are provided in the R&D Systems Catalog (1999) and (2000) R&D Systems Inc., 614 McKinley Place N.E. Minn. 55413, the R&D online catalog at www.rndsystems.com (e.g., Oct. 10, 1999), both of which are incorporated by reference for all purposes, the CFB (Cytokine Facts Book, 1994, Academic Press Ltd.), Chemokine Facts Book, 1997, Academic Press Ltd., incorporated by reference for all purposes, and the GenBank protein sequence database http://www.ncbi.nlm.nih.gov/entrez/query.fcgi).

A. SLC/6-Ckine
Campbell, J. J. et al., (1998) J. Cell Biol. 141(4):1053.
Hedrick, J. A. and A. Zlotnik. (1997) J. Immunol. 159:1589.
Hromas, R. et al., (1997) J. Immunol. 159:2554.
Kim, C. H. and H. E. Broxmeyer. (1999) J. Leuk. Biol. 65:6.
Nagira, M. et al., (1997) J. Biol. Chem. 272:19518.
Yoshida, R. et al., (1998) J. Biol. Chem. 273(12):7118.
Zlotnik, A. et al., (1999) Crit. Rev. Immunol. 19:1.

B. ELC/MIP-3β
Rossi, D. L. et al., (1997) J. Immunol. 158:1033.
Rollins, B. J. (1997) Blood 90(3):909.
Yoshida, R. et al., (1997) J. Biol. Chem. 272:13803.

C. TECK
Nomiyama, H. et al., (1998) Genomics 51(2):311.
Vicari, A. P. et al., (1997) Immunity 7:291.
Zaballos, A. et al., (1999) J. Immunol. 162(10):5671.
Zlotnik, A. et al., (1999) Crit. Rev. Immunol. 19:1.

D. CTACK/CCL27/ALP/ILC/ESkine
Morales et al., 1999, Proc Natl Acad Sci USA 96:14470–5.
Jarmin et al., 2000, J Immunol. 164:3460–4.
Baird et al., 1999, J Biol Chem. 274:33496–503.
Ishikawa-Mochizuki et al., 1999, FEBS Lett. 460:544–8.
Hromas et al., 1999, Biochem Biophys Res Commun. 258: 737–40.
Pan et al., 2000, J Immunol. 165:2943–49.
Homey et al., J Immunol. 164:3465–70.

E. BLC-1/BCA-1
Forster, R. et. al. (1996) Cell 87:1037.
Gunn, M. D. et al., (1998) Nature 391:799.
Legler, D. F. et al., (1998) J. Exp. Med. 187:655.

F. vMIPII
Boshoff et al., (1997) Science 278:290–4.
Kledal et al., (1997) Science 277:1656–9.
Sozzani et al., (1998) Blood 92:4036–9.
Geras-Raaka et al., (1999), Biochem Biophys Res Commun. 253:725–7.

G. MCP-4
Kim, C. H. and H. E. Broxmeyer. (1999) J. Leuk. Biol. 65:6.
Ruffing, N. et al., (1998) Cell Immunol. 189(2):160.
Uguccioni, M. et al., (1996) J. Exp. Med. 183:2379.
Zlotnik, A. et al., (1999) Crit. Rev. Immunol. 19:1.

H. mMIP-1γ (CCF18)
Wang et al., J Clin Immunol (1998) 18:214–22.
Hara et al., J Immunol. (1995) 155:5352–8.

XII. EXAMPLES

The following examples are offered to illustrate, but not to limit the claimed invention. Some experiments are described in Gosling et al., 2000, J. Imm. 164:2851–56, which is incorporated herein in its entirety for all purposes.

A. Abbreviations

EST, expressed sequence tag; ORF, open reading frame; DC, dendritic cell; ELC, EBI1 ligand chemokine; SLC, secondary lymphoid-tissue chemokine; TECK, thymus expressed chemokine; HEK293, human embryonic kidney 293 cells; PEI, polyethylenemine; CCR, CC chemokine receptor.

B. Materials and Methods

Human, viral and murine recombinant chemokines were obtained from R&D Systems (Minneapolis, Minn.; http://cytokine.rndsystems.com/cyt_cat/cyt_cat.html). $^{125}$I-labeled ELC and TECK were obtained from Amersham. Full length CCX CKR expression constructs were made in pIRESpuro expression vector (Clontech, Palo Alto, Calif.) with a FLAG epitope tag and prolactin signal sequence, and used to generated stable transfectants in HEK293 cells. Transient and stable transfections for CCX CKR and stalkokines were done using Superfect reagent (Qiagen, Valencia, Calif.) following manufacturer's protocol. Stables were generated by selecting in 2 ug/mL puromycin for 7 days, and expression was confirmed by FACS analysis of the FLAG epitope using anti-FLAG M1 (Sigma, St. Louis, Mo.) and 2' anti-mouse PE conjugate (Coulter Immunotech, Miami, Fla.).

Example 1

Identification and Cloning of CCX CKR

BLAST analysis of known chemokine receptors identified a bovine receptor, PPR1, designated as a gustatory receptor (Matsuoka et al., 1993, Biochem Biophys Res Comm 194: 540–11). A search of a human EST database using the PPR1 sequence identified two non-contiguous EST's: H67224 and AI131555. Primers were designed against the 5' end of H67224 (5' AAT TTG GCT GTA GCA GAT TTA CTC C 3' [SEQ. ID. NO:4]) and in the reverse orientation for the 3' end of AI131555 (5' GCT AAA AGT ACT GGT TGG C 3'[SEQ. ID. NO:5]), and used in PCR (5% DMSO, annealing 58° C.) of genomic DNA isolated from human buffy coats. The reaction resulted in a 855 bp product containing the ESTs and connecting sequences. The 855 bp fragment product was used to design additional primers for use in an anchored PCR screen of a Rapid Screen™ arrayed spleen cDNA library (Origene, Rockville, Md.), yielding a 5' extended clone; this clone was finally used to screen a human genomic library by filter hybridization. Full length coding sequence was deduced by sequence analysis of genomic clones using reverse primer from the 5' sequence of Origene clone PCR with proofreading Pfu (Stratagene) enzyme. The refined sequence was confirmed on several clones and is shown in FIG. 1. [A preliminary sequence determination differed from FIG. 1 at the following positions: 47, 64, 78, 120, 131, 545, 571, 574 (using the numbering of FIG. 1) which were G, G, G, C, C, T, A, and T, respectively [SEQ. ID. NO:3], which variant is also contemplated by the invention). The coding sequence was cloned into pIRESpuro expression vector (Clontech, Palo Alto, Calif.) with a FLAG epitope tag and prolactin signal sequence.

The deduced amino acid sequence encoded by the CCX CKR cDNA was compared to other human chemokine receptors using the sequence alignment program CLUSTAL (GeneWorks). Shown is the CCX CKR amino acid sequence aligned with the human CCR6, 7, 9 and orphan STRL33/Bonzo (FIG. 2A). The positions of the hydrophobic membrane spanning regions TM1 to TM7 are indicated by bars above the sequence. Amino acids identical between CCX CKR and other chemokine receptors are boxed. Multiple sequence alignment of the protein encoded by CCX CKR with these and other human chemokine receptor sequences showed amino acid identities ranging from 29 to 35%.

Example 2

Expression of CCX CKR in Leukocytes and Various Tissues

The expression of CCX CKR mRNA was determined by PCR analysis of human cDNAs as well as by RT-PCR of RNAs isolated from various tissues. First, CCX CKR expression in hematopoietic cells and tissues was investigated. Receptor expression was apparent in immature dendritic cells (DC) (derived from monocytes after treatment with GM-CSF and IL-4), primary T cells from 2 of 3 donors, and in spleen and lymph node tissue (FIG. 2B). Additionally, expression was detected in non-lymphoid tissues such as heart, kidney, placenta, trachea, and brain; unfractionated leukocytes on the same panel were also positive (FIG. 2B). Control PCR products for GAPDH confirmed the integrity of all starting RNA.

The observed pattern of CCX CKR overlaps with, and expands, the distribution reported for human expressed sequence tags found in the NCBI databases: These ESTs have been have been isolated from kidney, fetal heart, olfactory epithelium, and tonsillar B cells. Thus, CCX CKR seems expressed in motile cells in the periphery, as well as in lymphoid and non-lymphoid tissues.

Example 3

Stable Expression of CCX CKR Protein

To assess the functional properties of the protein encoded by the CCX CKR cDNA, including its potential chemokine binding profile, we constructed expression plasmids encoding CCX CKR with an added N-terminal Flag epitope. This allowed for detection and selection, using an anti-Flag mAb, of the most highly expressing stable transfectants. Human embryonic kidney 293 (HEK293) cells stably expressing the M1 flag epitope-tagged CCX CKR were confirmed by FACS (FIG. 2C), and were selected for further analysis. Cell lines transfected with the Flag-CCX CKR fusion plasmid are referred to as "F-CCR10 cells" (e.g., F-CCR10 293 cells).

Example 4

Adhesion of CCX CKR Transfectants to ELC-Stalkokines

A. Receptor Interrogation by Adhesion to Stalkokines.

"Stalkokine" technology was used to identify the chemokines bound by the CCX CKR. Briefly, immobilized native chemokines alone are incapable of capturing cells bearing cognate receptors (Imai et al., 1997, *Cell* 91:521). We have developed non-native chemokine structures, stalkokines, comprising chemokine moieties engineered as N-terminal attachments to extended modified mucins (Bazan et al., 1997, *Nature* 385:640). In one embodiment, stalkokines, harvested in the supernatants of HEK293 cells after transient transfection, are anchored to solid substrates via antibodies against carrier domains (e.g. poly-His epitopes) engineered to the carboxyl terminus, leaving the chemokine domain free to interact with candidate orphan receptors.

It will be appreciated that, in addition to identification of ligands bound by the CCX CKR, the stalkokine technology may be used for to identify ligands for other receptors (e.g., orphan chemokine receptors) via adhesion.

To determine ligand binding to CCX CKR, HEK293-CCX CKR cells were used to interrogate chemokine 'stalkokines' (SK), i.e., molecules in which discrete chemokine domains were engineered to be tethered to the end of an extended stalk structure. Stalkokines were interrogated using 8-well chamber slides coated first with anti-His anchoring antibody (10 ug/ml in PBS overnight at RT), which were washed and 'blocked' (2% FBS/0.5% BSA in PBS); treated with 250 ul of HEK293 cell stalkokine supernatants (1 hr at 37 C), and incubated with 500,000 HEK293-CCX CKR transfectants (1.5 hrs at RT). Inhibition of adhesion by competition with soluble chemokines was done by incubating cells with 5–10 ug/ml of recombinant chemokines. In all cases, nonadherent cells were removed by washing in PBS; remaining adherent cells were fixed with 1% glutaraldehyde, photoimaged and counted. As a primary screen this adhesion would reveal putative receptor-ligand interactions.

Figure 3A:
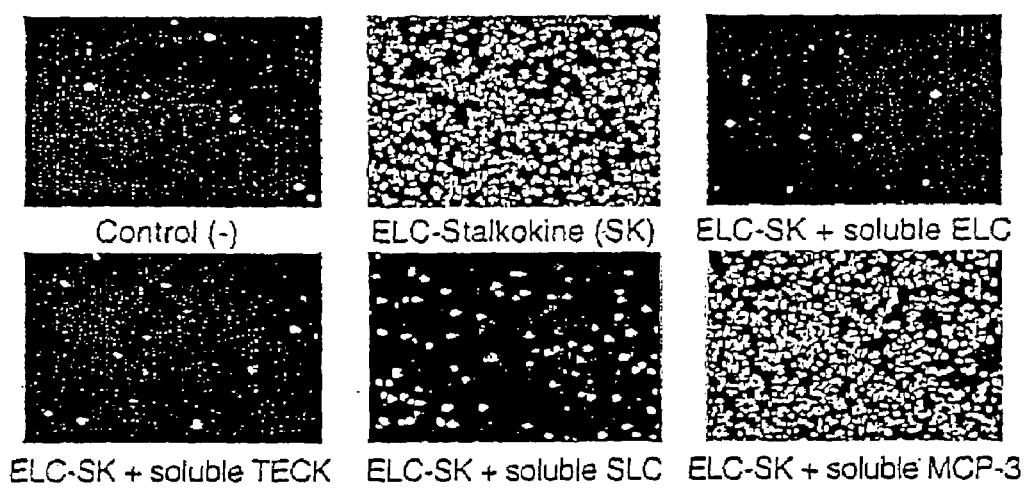
FIG. 3A shows interrogation of immobilized stalkokine (SK) by HEK293-CCX CKR cells, where 'control'=background adhesion of HEK293-CCX CKR cells to wells containing no stalkokine (anchoring antibodies and media are present); ELC-stalkokine (SK) =strong adhesion of HEK293-CCX CKR cells to locations containing ELC-stalkokines immobilized via anchoring antibodies; ELC-SK+soluble ELC, soluble TECK, or soluble SLC=ablation of adhesion in the presence of excess concentrations of soluble recombinant 'native form' chemokines as shown; ELC-SK+soluble MCP-3=no diminution in adhesion in the presence MCP-3 as representative of many non-competing chemokines. Wild type HEK293 cells showed no adhesion to any of the sites (not shown).
Figure 3B:
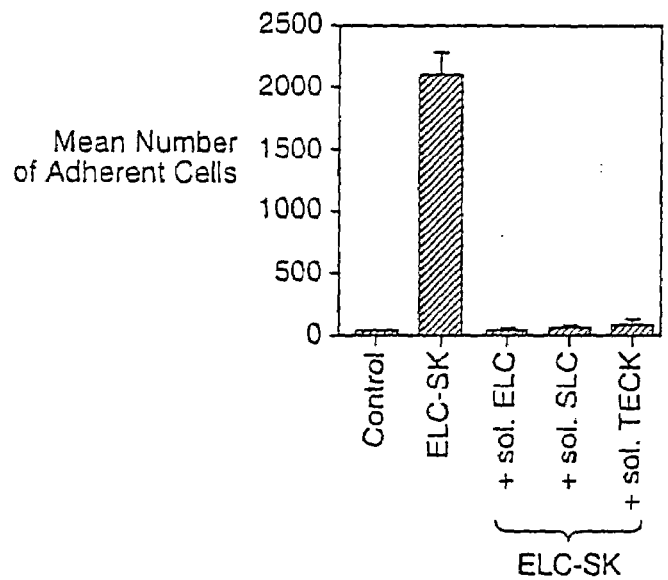
FIG. 3B shows the quantitation of adhesion of HEK293-CCX CKR cells to ELC-stalkokine in the absence and presence of soluble chemokines from a representative experiment.
Figure 3C:
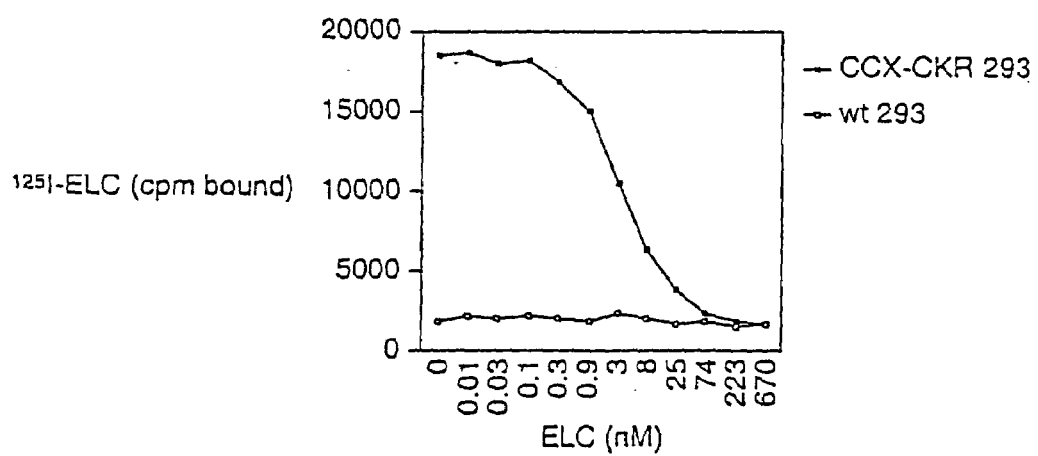
FIG. 3C shows the results of homologous competition binding assay using radiolabeled ELC in the presence of increasing concentrations of cold ELC on either HEK293-CCX CKR cells (filled squares) or wild type HEK293 cells (open squares).

CCX CCR cells adhered very well to ELC stalkokines (ELC-SK; FIG. 3A). Furthermore ELC-SK mediated adhesion was abolished in the presence of soluble native ELC as a competitor (FIG. 3A, top row). We also observed a significant reduction in ELC-SK mediated adhesion of HEK293-CCX CKR cells in the presence of soluble SLC, as well as soluble TECK, but not soluble MCP-3 (FIG. 3A, bottom row). These experiments were performed and quantitated over several independent trials, an example of which is given in FIG. 3B, and were found to be highly reproducible. Moreover, radiolabeled ELC was used in a traditional homologous competition assay in the presence of increasing concentrations of unlabeled ELC. The results revealed significant binding of ELC to HEK293-CCX CKR cells, but not to wildtype (wt) HEK293 cells (FIG. 3C). Nearly identical results were obtained in homologous competition of radiolabeled TECK with cold TECK (not shown). Taken together, the stalkokine-based adhesion and radiolabeled ligand binding/homologous competition assays indicate that CCX CKR is a new chemokine receptor that bound a novel compliment of chemokines.

Example 5

Complete Ligand Binding 'Fingerprint' of CCX CKR

In order to rapidly and thoroughly define a given chemokine receptor's ligand binding fingerprint, we have established an approach to comprehensively profile chemokine receptors using a large array of purified chemokines and chemokine variants. We used this approach to confirm independently the interaction of ELC and other chemokines with CCX CKR. Employing radioligand binding of $^{125}$-labeled-ELC or $^{125}$-TECK to CCX CKR stable transfectants, chemokine specificity for the new receptor was determined. Approximately 80 distinct purified chemokines and chemokine variants were used as cold competitors (initially at a saturating final concentration of 200 nM), against $^{125}$-labeled ELC (FIG. 4A) or $^{125}$-TECK (not shown) in binding experiments; the results were comparable for each. The radiolabeled ligand binding displacement data confirmed that CCX CKR bound well to human and murine ELC, SLC, TECK, and moderately to mMIP-1gamma (although its human homolog did not bind). Moreover, other potential lower affinity chemokine ligands were revealed including the CXC chemokine BLC, and the virally-encoded vMIPII from the human Kaposi's sarcoma herpesvirus HHV8 (FIG. 4A). All other chemokines tested failed to compete consistently with radiolabeled ELC.

Example 6

Determination of Binding Constants

Binding analysis was carried out using efficiency-maximized radioligand binding utilizing filtration protocols designated "Displace Max" (Dairaghi et al., 1999, *J. Biol. Chem.* 274:21569). In these assays, DisplaceMax employed the simultaneous interrogation of CCX CKR transfectants by >80 distinct purified chemokines in the ability to displace radiolabeled ELC or TECK, using the protocol described (Dairaghi et al., 1999, *J. Biol. Chem.* 274:21569).

Figure 4B:
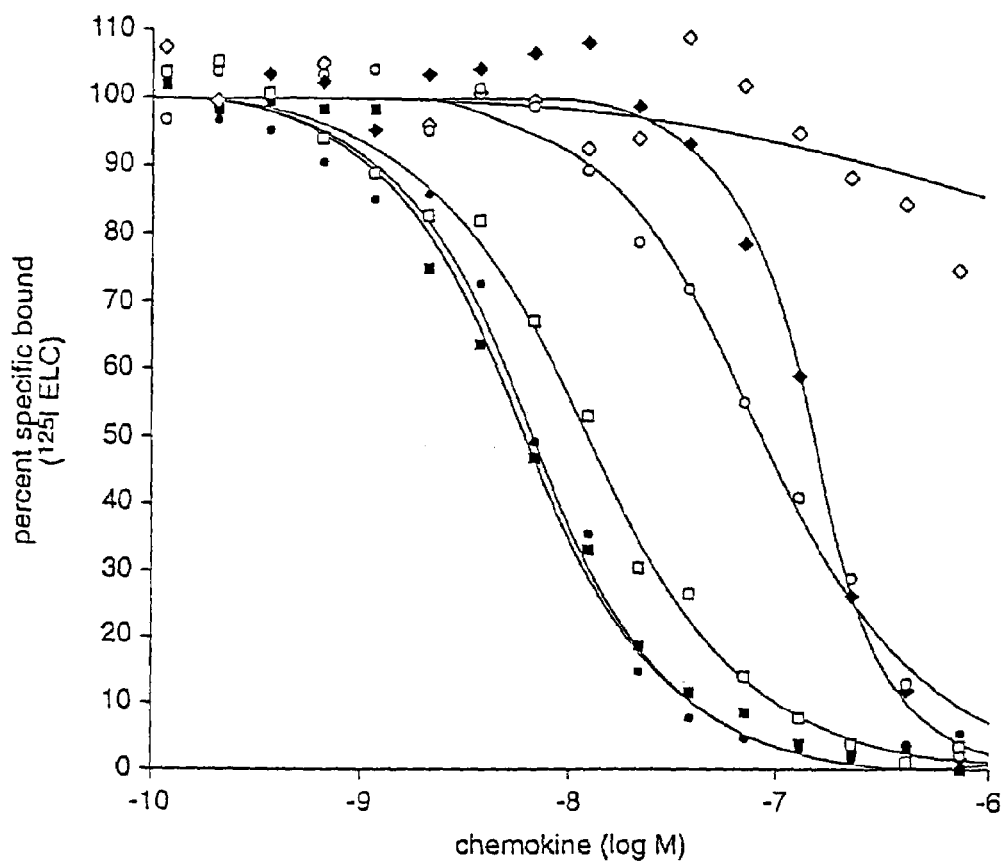

The binding interactions identified in the primary screen were examined quantitatively by extensive radioligand binding competition to CCX CKR stable transfectants and Scatchard transformation of the displacement data (FIG. 4B). The results confirmed the high affinity binding of human ELC, SLC, and TECK with affinities between ~Kd 5–15 nM. In each case, the murine versions of these chemokines also bound, and with even greater affinity; the apparent Kd's are listed in FIG. 4B. Intriguingly, the CC chemokine BLC, while of lesser affinity, also bound well, showing a steeply inflected competition curve. The viral chemokine vMIP-II showed moderate to low affinity, and was the only viral chemokine to show any interaction with CCX CKR. In similar experiments, murine CTACK bound the receptor with a Kd of ~9 nM (not shown). CTACK is also referred to as CCL27, ALP, ILC, and ESkine.

The HEK293-CCX CKR cells did not exhibit robust cytoplasmic calcium signals in several tests, but this may be due to G protein dilution, since the transfectants stably express CCX CKR protein at >250,000 sites per cell (not shown). Also, in preliminary chemotaxis analyses, the CCX CKR transfectants showed moderate migration in response to ELC and SLC, but not to chemokines having no binding activity (not shown). Taken together, these data indicate that the physiologically relevant spectrum of ligands for CCX CKR includes ELC, SLC and TECK, with possible lower affinity interactions with the CXC chemokine BLC and the viral chemokine vMIP-II.

Example 7

Identification of Small Molecule Modulators of CCX CKR

This example illustrates screening procedures used in characterizing the compounds of the present invention.

Source plates of chemical libraries were obtained from commercial vendors and contained individual compounds at 5 mg/mL in DMSO, or in some instances, at 1 mg/mL. From these, multiple compound plates containing 10 compounds in each well were made, and these were diluted in 20% DMSO to a concentration of 50 µg/mL (10 µg/mL for those beginning at 1 mg/mL). An aliquot of 20 µL of each mixture was put into the test plates, which were stored frozen until use.

HEK293 cells stably expressing the M1 flag epitope-tagged CCX CKR (described in Example 3, supra) were cultured in DMEM-10% FBS, and harvested when the concentration was between 0.5–1.0×10$^6$ cells/mL. The cells were centrifuged and resuspended in assay buffer (20 mM HEPES, 80 mM NaCl, 1 mM CaCl$_2$, 5 mM MgCl$_2$, and with 0.2% bovine serum albumin, pH 7.4) to a concentration of 5.6×10$^6$ cells/mL.

Using a Multi-Probe automated system, 0.09 mL of cells was added to each well of the assay test plates containing the compounds, followed by 0.09 mL of $^{125}$I-MIPβ3/ELC (from Amersham Pharmacia Biotech) diluted in assay buffer (final concentration ~25–100 pM, with ~50,000 cpm per well). The final concentration of the compounds was 1–5 µg/mL each. The plates were sealed and incubated for approximately 3 hours at 4° C. on a shaker platform. The assay plates were harvested using Packard GP/B filter plates, pre-soaked in PEI solution, on the vacuum harvest apparatus. Scintillation fluid (50 µL) was added to each of the wells, the plates were sealed and counted in a Top Count scintillation counter. Control wells contained either diluent only (for total counts) or excess ELC (1 µg/mL, for non-specific binding) and were used to calculate the percent of total inhibition of ELC binding for each set of compounds. Compounds I and II were found to inhibit binding between ELC and CCX CKR. Compound III was determined to enhance binding.

Example 8

Ligand Induced Internalization of CCX CKR 293 cells transfected with the Flag-CCX CKR fusion plasmid (i.e., "293 F-CCR10 cells;" see Example 3) were incubated at 37° C. with varying concentrations of chemokines (ELC, SLC, TECK, murine CTACK and MCP-4) for 15 or 45 minutes. Following incubation, the cells were washed and fixed with 3% paraformaldehyde for 15 minutes on ice. The cells were stained with anti-Flag M1 antibody, followed by a PE-conjugated anti-mouse secondary antibody. FACS analysis were then carried out to determine surface expression of the receptor.

Figure 6A:
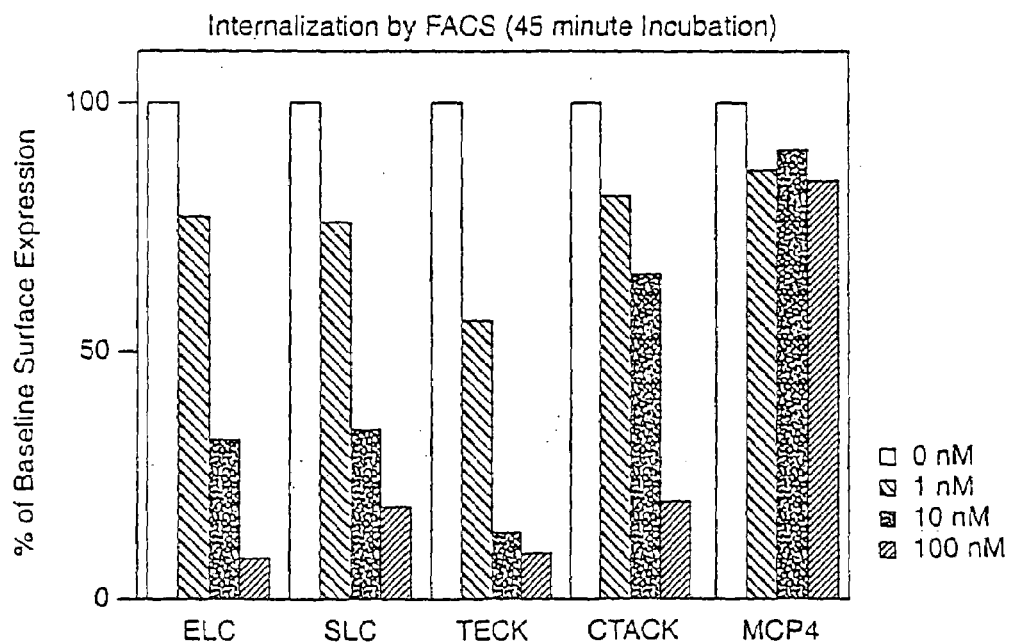
FIG. 6(A) shows FACS scans of cells incubated for 45 minutes in the presence or absence of chemokines (1 nM, 10 nM or 100 nM ELC, SLC, TECK, CTACK or MCP4), or an isotype antibody control.
Figure 6B:
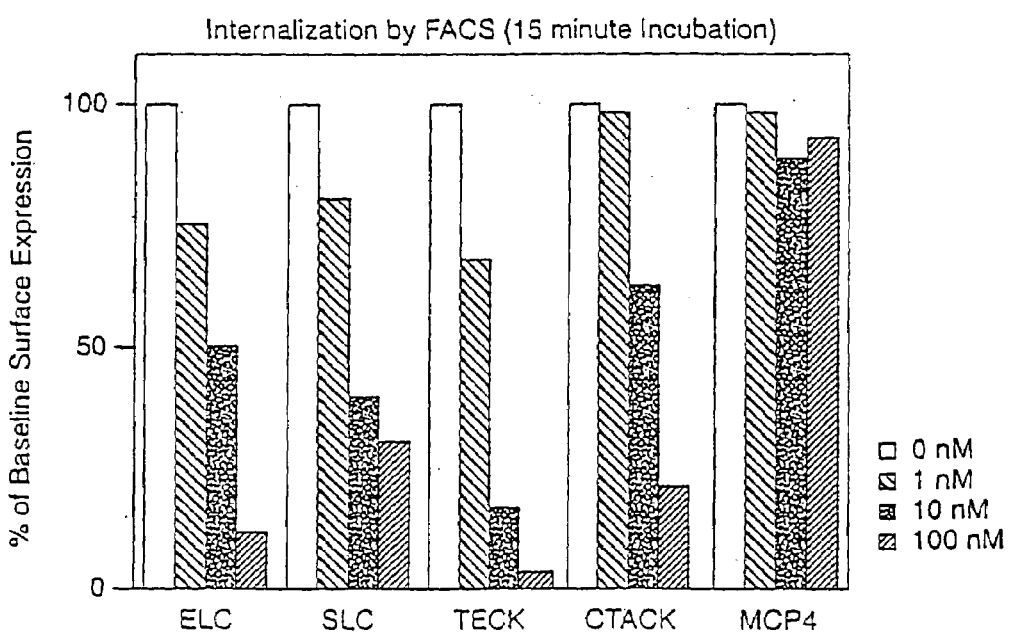
FIG. 6(B) shows the same experiment with a 15 minute incubation.

Results: A reduction in antibody binding in the presence of ligand is an indication of ligand-induced internalization of the receptor. Cells incubated with ligand on ice, and then washed, or incubated with primary antibody in the absence of ligand, showed no inhibition of antibody binding to the receptor on the surface of the cells (i.e., no receptor internalization; data not shown). Internalization of the receptor was observed in the presence of 100 nM ELC, SLC, TECK, and murine CTACK (see FIG. 6). MCP-4 did not cause internalization. Internalization of the receptor was found to be dose and time dependent.

All references cited herein are incorporated herein by reference in their entirety and for all purposes to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A process for providing a pharmaceutical composition, comprising:
   (a) identifying a modulator of the binding of CCX CKR polypeptide to a chemokine comprising
      (i) contacting an isolated or recombinant CCX CKR polypeptide having the amino acid sequence as set forth in SEQ ID NO:2, or a fragment or variant thereof, and the chemokine in the presence of a test compound, and
      (ii) comparing the level of binding of the chemokine and the polypeptide in the presence of the test compound with the level of binding in the absence of the test compound, wherein
      the CCX CKR polypeptide, fragment or variant can bind the chemokine in the absence of test compound and the variant has at least 90% sequence identity to SEQ ID NO:2,
      the chemokine is selected from the group consisting of ELC (EBI-1-ligand chemokine), SLC (secondary lymphoid organ chemokine), TECK (thymus expressed chemokine), BLC (B-lymphocyte chemoattractant), CTACK (cutaneous T cell attracting chemokine), mMIP-1γ (murine macrophage inflammatory protein 1γ) and vMIPII (viral macrophage inflammatory protein II), and
      a decrease in binding indicates that the test compound is an inhibitor of binding and an increase in binding indicates that the test compound is an enhancer of binding; and
   (b) formulating the modulator identified in (a) as a pharmaceutical composition.

2. The method of claim 1, wherein said contacting comprises contacting a cell expressing the CCX CKR polypeptide, fragment or variant.

3. The method of claim 1, wherein the CCX CKR polypeptide, fragment or variant is part of a cell fraction.

4. The method of claim 1, wherein the chemokine is ELC.

5. The method of claim 1, wherein the chemokine is SLC.

6. The method of claim 1, wherein the chemokine is TECK.

7. The method of claim 1, wherein the chemokine is BLC.

8. The method of claim 1, wherein the chemokine is CTACK.

9. The method of claim 1, wherein the chemokine is mMIP-1γ.

10. The method of claim 1, wherein the chemokine is vMIPII.

11. The method of claim 1, wherein the variant has at least 95% sequence identity to SEQ ID NO:2.

12. The method of claim 11, wherein the variant has at least 98% sequence identity to SEQ ID NO:2.

13. The method of claim 12, wherein the CCX CKR polypeptide has the amino acid sequence of SEQ ID NO:2.

14. The method of claim 1, wherein formulating comprises combining the modulator with a pharmaceutically acceptable carrier.

* * * * *